US011389403B2

(12) United States Patent
Van Der Beek et al.

(10) Patent No.: US 11,389,403 B2
(45) Date of Patent: *Jul. 19, 2022

(54) INFANT FORMULA WITH SPECIAL LIPID ARCHITECTURE FOR PROMOTING HEALTHY GROWTH

(71) Applicant: N.V. Nutricia, Zoetermeer (NL)

(72) Inventors: Eline Marleen Van Der Beek, Utrecht (NL); Marieke Abrahamse-Berkeveld, Utrecht (NL); Dennis Stanley Acton, Utrecht (NL); Stefanie Schoen, Utrecht (NL)

(73) Assignee: N.V. NUTRICIA, Zoetermeer (NL)

( * ) Notice: Subject to any disclaimer, the term of this patent is extended or adjusted under 35 U.S.C. 154(b) by 78 days.

This patent is subject to a terminal disclaimer.

(21) Appl. No.: 15/768,195

(22) PCT Filed: Oct. 14, 2016

(86) PCT No.: PCT/EP2016/074810
§ 371 (c)(1),
(2) Date: Apr. 13, 2018

(87) PCT Pub. No.: WO2017/064304
PCT Pub. Date: Apr. 20, 2017

(65) Prior Publication Data
US 2018/0296481 A1 Oct. 18, 2018

(30) Foreign Application Priority Data
Oct. 15, 2015 (EP) .................................. 15190039

(51) Int. Cl.
*A61K 9/10* (2006.01)
*A23L 33/00* (2016.01)
*A23L 33/115* (2016.01)
*A23L 33/17* (2016.01)
*A23L 33/125* (2016.01)
*A61K 31/685* (2006.01)
*A61K 31/7016* (2006.01)
*A61K 31/702* (2006.01)
*A61K 35/60* (2006.01)
*A61K 35/66* (2015.01)
*A61K 36/28* (2006.01)
*A61K 36/31* (2006.01)
*A61K 36/889* (2006.01)
*A61K 38/17* (2006.01)

(52) U.S. Cl.
CPC .............. *A61K 9/10* (2013.01); *A23L 33/115* (2016.08); *A23L 33/125* (2016.08); *A23L 33/17* (2016.08); *A23L 33/40* (2016.08); *A61K 31/685* (2013.01); *A61K 31/702* (2013.01); *A61K 31/7016* (2013.01); *A61K 35/60* (2013.01); *A61K 35/66* (2013.01); *A61K 36/28* (2013.01); *A61K 36/31* (2013.01); *A61K 36/889* (2013.01); *A61K 38/1709* (2013.01); *A23V 2002/00* (2013.01)

(58) Field of Classification Search
CPC combination set(s) only.
See application file for complete search history.

(56) References Cited

U.S. PATENT DOCUMENTS

| 5,709,888 | A | 1/1998 | Gil et al. |
|---|---|---|---|
| 7,776,332 | B1 | 8/2010 | Kuslys et al. |
| 8,883,219 | B2 | 11/2014 | Van Der Beek et al. |
| 9,320,294 | B2 * | 4/2016 | van Baalen .......... A61K 31/201 |
| 9,345,259 | B2 | 5/2016 | Van Der Beek et al. |
| 9,532,966 | B2 * | 1/2017 | Van Der Beek ..... A61K 31/201 |
| 9,649,286 | B2 * | 5/2017 | Van Der Beek ..... A61K 31/201 |
| 2002/0004527 | A1 | 1/2002 | Auestad et al. |
| 2003/0104078 | A1 | 6/2003 | Barrett-Reis et al. |
| 2004/0022922 | A1 | 2/2004 | Rutenberg |
| 2004/0062820 | A1 | 4/2004 | Lasekan et al. |
| 2005/0037089 | A1 | 2/2005 | Jobbins |
| 2005/0214392 | A1 | 9/2005 | McPeak et al. |
| 2006/0188614 | A1 | 8/2006 | Shapira |
| 2006/0210697 | A1 | 9/2006 | Mower |
| 2007/0073193 | A1 | 3/2007 | Park |
| 2007/0073194 | A1 | 3/2007 | Chen et al. |
| 2008/0003330 | A1 | 1/2008 | Rueda et al. |
| 2008/0064656 | A1 | 3/2008 | Van Tol |
| 2008/0292724 | A1 | 11/2008 | Hageman et al. |
| 2009/0011075 | A1 | 1/2009 | Shulman et al. |
| 2009/0136615 | A1 | 5/2009 | Speelmans et al. |
| 2009/0186803 | A1 | 7/2009 | Zwijsen et al. |
| 2011/0206743 | A1 | 8/2011 | Van Baalen et al. |
| 2011/0217411 | A1 | 9/2011 | Van Der Beek et al. |
| 2011/0294757 | A1 | 12/2011 | Shulman et al. |

(Continued)

FOREIGN PATENT DOCUMENTS

EP 0 333 288 A1 9/1989
EP 1 252 824 A2 10/2002

(Continued)

OTHER PUBLICATIONS

U.S. Appl. No. 15/259,537, US 2017-0151203.
U.S. Appl. No. 15/033,471, US 2016-0263033.
U.S. Appl. No. 15/503,930, US 2017-0173343.
U.S. National Phase of PCT/EP2016/074815, Unpublished.
"Glycosphingolipid," as accessed Oct. 5, 2015, from https://en.wikipedia.org/wiki/Glycosphingolipid.
Agostoni et al., "Polyunsaturated Fatty Acids in Human Milk and Neurological Development in Breastfed Infants," Current Pediatric Reviews, 1:25-30 (2005).
Andres et al., "Body fat and bone mineral content of infants fed breast milk, cow's milk formula, or soy formula during the first year of life", The Journal of Pediatrics, 2013, vol. 163, No. 1, pp. 49-54.
Benoit et al., "Phospholipid Species and Minor Sterols in French Human Milks in Breast Fed Infants," Food Chemistry, 120:684-691 (2010).

(Continued)

Primary Examiner — Hasan S Ahmed
(74) Attorney, Agent, or Firm — Foley & Lardner LLP

(57) ABSTRACT

The present invention relates to formulae for infants comprising large lipid globules and/or lipid globules with a coating of phospholipids for rendering the growth trajectory or body development during the first year of life more similar to that observed for human milk fed infants.

22 Claims, 3 Drawing Sheets

(56) References Cited

U.S. PATENT DOCUMENTS

| | | |
|---|---|---|
| 2011/0300204 A1 | 12/2011 | Van Der Beek et al. |
| 2011/0300225 A1 | 12/2011 | Van Der Beek et al. |
| 2012/0035274 A1 | 2/2012 | Park |
| 2012/0039852 A1 | 2/2012 | Darimont-Nicolau et al. |
| 2012/0148588 A1 | 6/2012 | Knopf et al. |
| 2013/0052297 A1 | 2/2013 | Van De Heijning et al. |
| 2013/0071446 A1 | 3/2013 | Van Der Beek et al. |
| 2013/0096087 A1 | 4/2013 | Van Der Beek et al. |
| 2014/0093554 A1 | 4/2014 | Van Der Beek et al. |
| 2014/0162223 A1 | 6/2014 | Saavedra et al. |
| 2015/0306117 A1 | 10/2015 | Van Der Beek et al. |
| 2016/0015068 A1 | 1/2016 | Ao et al. |
| 2016/0205983 A1 | 7/2016 | Van Baalen et al. |
| 2016/0219915 A1 | 8/2016 | Van Der Beek et al. |

FOREIGN PATENT DOCUMENTS

| | | |
|---|---|---|
| EP | 1 800 675 A1 | 6/2007 |
| EP | 2 305 049 | 4/2011 |
| EP | 2 465 359 | 6/2012 |
| EP | 2 583 562 A1 | 4/2013 |
| EP | 2 825 062 B1 | 1/2015 |
| JP | 2001-158736 | 6/2001 |
| SU | 1084006 A | 4/1984 |
| WO | WO-98/44917 A1 | 10/1998 |
| WO | WO-03/005836 A2 | 1/2003 |
| WO | WO-2005/007373 A1 | 1/2005 |
| WO | WO-2005/051091 A1 | 6/2005 |
| WO | WO-2005/051092 A2 | 6/2005 |
| WO | WO-2005/063050 A1 | 7/2005 |
| WO | WO-2006/052134 A2 | 5/2006 |
| WO | WO-2006/094995 A1 | 9/2006 |
| WO | WO-2006/114790 A2 | 11/2006 |
| WO | WO-2007/039596 A1 | 4/2007 |
| WO | WO-2007/073192 A2 | 6/2007 |
| WO | WO-2007/073193 A2 | 6/2007 |
| WO | WO-2007/073194 A2 | 6/2007 |
| WO | WO-2007/097523 A2 | 8/2007 |
| WO | WO-2008/005033 A1 | 1/2008 |
| WO | WO-2008/054192 A1 | 5/2008 |
| WO | WO-2008/071667 A1 | 6/2008 |
| WO | WO-2008/081934 A1 | 7/2008 |
| WO | WO-2009/051502 A1 | 4/2009 |
| WO | WO-2009/057121 A1 | 5/2009 |
| WO | WO-2009/066685 A1 | 5/2009 |
| WO | WO-2009/138680 A2 | 11/2009 |
| WO | WO-2009/1 54448 A1 | 12/2009 |
| WO | WO-2010/027258 A1 | 3/2010 |
| WO | WO-2010/027259 A1 | 3/2010 |
| WO | WO-201 0/068105 A1 | 6/2010 |
| WO | WO-201 0/070613 A2 | 6/2010 |
| WO | WO-2010/068086 A1 | 6/2010 |
| WO | WO-2010/068103 A1 | 6/2010 |
| WO | WO-2010/134810 | 11/2010 |
| WO | WO-2011/071371 A1 | 6/2011 |
| WO | WO-2011/108918 | 9/2011 |
| WO | WO-2011/108934 A1 | 9/2011 |
| WO | WO-2011/115476 | 9/2011 |
| WO | WO-2011/115491 | 9/2011 |
| WO | WO-2011/138457 | 11/2011 |
| WO | WO-2012/173467 A1 | 12/2012 |
| WO | WO-2012/173486 | 12/2012 |
| WO | WO-2013/036102 A1 | 3/2013 |
| WO | WO-2013/036103 A1 | 3/2013 |
| WO | WO-2013/036104 A1 | 3/2013 |
| WO | WO-2013/036123 A | 3/2013 |
| WO | WO-2013/153071 A2 | 10/2013 |
| WO | WO-2013/191533 A1 | 12/2013 |
| WO | WO-2015/014967 A1 | 2/2015 |
| WO | WO-2015/065193 A1 | 5/2015 |
| WO | WO-2015/067325 | 5/2015 |
| WO | WO-2015/078505 A1 | 6/2015 |
| WO | WO-2015/091789 A2 | 6/2015 |
| WO | WO-2016/024864 A1 | 2/2016 |
| WO | WO-2017/064304 A1 | 4/2017 |

OTHER PUBLICATIONS

Database WPI Week 200937, Thompson Scientific, London, GB, An 2009-J69887, May 28, 2009, XP002578379.
Dewey et al., "Breast-fed infants are leaner than formula-fed infants at 1 y of age: the DARLING study", Am J Clin Nutr, 1993, vol. 57, pp. 140-145.
Dewey et al., "Growth of breast-fed and formula-fed infants from 0 to 18 months: The DARLING study", Pediatrics, Jun. 1992, vol. 89, No. 6, pp. 1035-1041.
Durand et al., "Particle Sizes and Stability of UHT Bovine, Cereal and Grain Milks," Food Hydrocolloids, 17:671-678 (2003).
Fave et al., "Physicochemical Properties of Lipids; New Strategies to Manage Fatty Acid Bioavailability," Cellular and Molecular Biology, 50(7):815-831 (2004).
Fox, http://www.foxnews.com/health/2014/05/29/30-percent-world-is-now-overweight-or-obese-no-country-immune.html, accessed on Sep. 21, 2016.
Hamilton, "Interactions of Triglycerides with Phospholipids; Incorporation into the Bilayer Structure and Formation of Emulsions," Biochemistry, 28:2514-2520 (1989).
Holman et al., "Deficiency of Essential Fatty Acids and Membrane Fluidity During Pregnancy and Lactation," Proceedings of the National Academy of Sciences of the United States of America, 88(11):4835-4839 (1991).
Hur et al., "Influence of Initial Emulsifier Type on Microstructural Changes Occurring in Emulsified Lipids During In Vitro Digestion," Food Chemistry, 114:253-262 (2009).
InFat—The premium choice for infant formula—closer to mother's milk, Nov. 2009, AAK Magazine.
International Preliminary Report on Patentability in Application No. PCT/NL2009/050343 dated Jul. 19, 2010.
International Preliminary Report on Patentability in Application No. PCT/NL2011/050156 dated Aug. 24, 2012.
International Preliminary Report on Patentability in Application No. PCT/NL2011/050187 dated Jun. 13, 2012.
International Preliminary Report on Patentability in Application No. PCT/NL2011/050188 dated Jun. 15, 2012.
International Preliminary Report on Patentability dated Sep. 17, 2013 in International Application No. PCT/NL2012/050623.
International Search Report for PCT/NL2008/050792 dated Jul. 8, 2009.
International Search Report in Application No. PCT/NL2009/050343 dated Jul. 15, 2009.
International Search Report in Application No. PCT/NL2009/050525 dated Dec. 1, 2009 (3 pages).
International Search Report in Application No. PCT/NL2009/050526 dated Dec. 14, 2009.
International Search Report in Application No. PCT/NL2009/050754 dated May 7, 2010.
International Search Report in Application No. PCT/NL2009/050756 dated May 11, 2010.
International Search Report in Application No. PCT/NL2011/050156 dated Jun. 1, 2011.
International Search Report in Application No. PCT/NL2011/050187 dated Jul. 5, 2011.
International Search Report in Application No. PCT/NL2011/050188 dated Jul. 5, 2011.
International Search Report in PCT/NL2010/050108 dated Nov. 11, 2010.
International Search Report in PCT/NL2010/050142 dated Mar. 2, 2011.
International Search Report issued in International Patent Application No. PCT/EP2016/074810, dated Dec. 13, 2016.
International Search Report issued in International Patent Application No. PCT/EP2016/074815, dated Jan. 4, 2017.
International Search Report issued in International Patent Application No. PCT/US2015/050580 dated Dec. 18, 2015.
International Search Report issued International Patent Application No. PCT/NL2014/050761, dated Jan. 26, 20150.
International Search Report dated Oct. 30, 2012 in International Application No. PCT/NL2012/050623.

(56) References Cited

OTHER PUBLICATIONS

International Search Report of PCT/NL2013/050431 dated Sep. 30, 2013.
Jensen et al., "Specialty Lipids for Infant Nutrition. I. Milks and Formulas," Journal of Pediatric Gastroenterlogy and Nutrition, 15(3):232-245 (1992).
Joscelyne et al., "Food Emulsions Using Membrane Emulsification; Conditions for Producing Small Droplets," Journal of Food Engineering, 39:59-64(1999).
Koletzko et al., "Lower protein in infant formula is associated with lower weight upto age 2 y: a randomized clinical trial", Am J Clin Nutr, 2009, vol. 89, pp. 1836-1845.
Lucas Alan, "Long-Term Programming Effects of Early Nutrition—Implications for the Preterm Infant", Journal of Perinatology (2005) 25, S2-S6.
Makrides et al., "Fatty Acid Composition of Brain, Retina, and Erythrocytes in Breast- and Formula-Fed Infants," American Journal of Clinical Nutrition (US), 60(2):189-194 (1994).
Marmot, et al. "Effect of breast-feeding on plasma cholesterol and weight in young adults", Journal of Epidemiology and Community Health (1980), vol. 34, pp. 164-167.
McClements, "Food Emulsions—Principles, Practices, and Techniques," CRC Press, Inc., Second Edition, Section 7.3 (2005).
Michalski et al., "Optical Parameters of Milk Fat Globules for Laser Light Scattering Measurements," Lait, 81(6):787-796 (2001).
Michalski et al., "Size Distribution of Fat Globules in Human Colostrum, Breast Milk, and Infant Formula," Journal of Dairy Science, American Dairy Science Association, 88:1927-1940 (2005).
Michalski et al., "The Dispersion State of Milk Fat Influences Triglyceride Metabolism in the Rat," European Journal of Nutrition, 44:436-444 (2005).
Michalski, "The Supramolecular Structure of Milk Fat Influences Plasma Triacylglycerols and Fatty Acid Profile in the Rat," European Journal of Nutrition, 45:215-224 (2006).
Mun et al., "Influence of Interfacial Composition on In Vitro Digestibility of Emulsified Lipids: Potential Mechanism for Chitosan's Ability to Inhibit Fat Digestion," Food Biophysics, 1:21-29 (2006).
Oddy, "Infant feeding and obesity risk in the child", Breastfeed Rev., Jul. 20112, vol. 20, No. 2, pp. 7-12.
Osteoporosis, PubMed Health, available at http;www.ncbi.nlm.nih.gov/pubmedhealth/PMH0001400, 2012.
Owen, et al. "Infant Feeding and Blood Cholesterol: A Study in Adolescents and a Systematic Review", Pediatrics (2006) vol. 110, pp. 597-608.
Park et al., "Influence of Encapsulation of Emulsified Lipids With Chitosan on Their In Vivo Digestibility," Food Chemistry, 104:761-767 (2007).
Petrowski, "Emulson Stability and Its Relation to Foods," Emulsion Stability, 309-359 (1976).
Ruegg et al., "The Fat Globule Size Distribution in Human Milk," Biochimica et Biophysica Acta, 666:7-14 (1981).
Schultz et al., "High-Pressure Homogenization as a Process for Emulsion Formation," Chemical Engineering Technology, 27(4):361-368 (2004).
Simonin et al., "Comparison of the Fat Content and Fat Globule Size Distribution of Breast Milk From Mothers Delivering Term and Preterm," The American Journal of Clinical Nutrition, 40:820-826 (1984).
Sprong et al., "Bovine milk fat components inhibit food-borne pathogens", International Dairy Journal, 2002, vol. 12, pp. 209-215.
Timby et al., "Neurodevelopment, nutrition, and growth until 12 mo of age in infants fed a low-energy, low-protein formula supplemented with bovine milk fat globule membranes: a randomized controlled trial", Am J Clin Nutr, 2014, 9 pages.
Vickers, et al., "Supplementation with a Mixture of Complex Lipids Derived from Milk to Growing Rats Results in Improvements in Parameters Related to Growth and Cognition," Nutrition Research, 29:426-435 (2009).
Whittlestone et al., "Variations in the Fat Content of Human Milk During Suckling," Ruakura Animal Research Station, Department of Agriculture, 204-206 (1953).
Agostoni et al., "Enteral Nutrient Supply for Preterm Infants: Commentary From the European Society for Paediatric Gastroenterology, Hepatology, and Nutrition Committee on Nutrition", Journal of Pediatric Gastroenterology and Nutrition, vol. 50, No. 1, Jan. 2010, pp. 85-91 (7 pages).
Butte et al., "Energy Expenditure and Deposition of Breast-Fed and Formula-Fed Infants during Early Infancy", Pediatric Research, vol. 28, No. 6, 1990, pp. 631-640 (10 pages).
Clausen et al., "Overweight and the Metabolic Syndrome in Adult Offspring of Women with Diet-Treated Gestational Diabetes Mellitus or Type 1 Diabetes", J Clin Endocrinol Metab, vol. 94, No. 7, Jul. 2009, pp. 2464-2470 (8 pages).
Eriksson et al., "Size at birth, childhood growth and obesity in adult life", International Journal of Obesity, vol. 25, 2001, pp. 735-740 (7 pages).
Gallier et al., "A novel infant milk formula concept: Mimicking the human milk fat globule structure", Colloids and Surfaces B: Biointerfaces, vol. 136, 2015, pp. 329-339 (11 pages).
Llewellyn et al., "Development and factor structure of the Baby Eating Behaviour Questionnaire in the Gemini birth cohort", Appetite, vol. 57, 2011, pp. 388-396 (9 pages).
Lubetzky et al., "Energy expenditure in human milk—versus formula-fed preterm infants", The Journal of Pediatrics, vol. 143, Issue 6, Dec. 2003, pp. 750-753 (4 pages).
Mallan et al., "Confirmatory factor analysis of the Baby Eating Behaviour Questionnaire and associations with infant weight, gender and feeding mode in an Australian sample", Appetite, vol. 82, Nov. 1, 2014, pp. 43-49 (7 pages).
Oken et al., "Gestational weight gain and child adiposity at age 3 years", American Journal of Obstetrics & Gynecology, vol. 196, Apr. 2007, pp. 322.e1-322.e8 (8 pages).
Rasmussen et al., "The relation of weight, length and ponderal index at birth to body mass index and overweight among 18-year-old males in Sweden", Abstract, European Journal of Epidemiology, vol. 14, Issue 4, Jun. 1998, pp. 373-380 (7 pages).
Snitker et al., "Effects of novel capsinoid treatment on fatness and energy metabolism in humans: possible pharmacogenetic implications", American Journal of Clinical Nutrition, vol. 89, 2009, pp. 45-50 (6 pages).
Sproston, et al., "Enzymatic Modification of Anhydrous Milkfat with n-3 and n-6 Fatty Acids for Potential Use in Infant Formula: Comparison of Methods", Journal of the American Oil Chemists' Society, vol. 93, 2016, pp. 251-265 (15 pages).
Stunkard et al., "Energy intake, not energy output, is a determinant of body size in infants", American Journal of Clinical Nutrition, vol. 69, 1999, pp. 524-530 (7 pages).
Young et al., "Biological Determinants Linking Infant Weight Gain and Child Obesity: Current Knowledge and Future Directions", Advances in Nutrition, vol. 3, 2012, pp. 675-686 (12 pages).

* cited by examiner

INFANT FORMULA WITH SPECIAL LIPID ARCHITECTURE FOR PROMOTING HEALTHY GROWTH

CROSS-REFERENCE TO RELATED APPLICATIONS

This application is the National Phase of International Patent Application No. PCT/EP2016/074810 filed Oct. 14, 2016, published on Apr. 20, 2017 as WO 2017/064304 A1, which claims priority to European Patent Application No. 15190039.6, filed Oct. 15, 2015. The contents of these applications are herein incorporated by reference in their entirety.

FIELD OF THE INVENTION

The invention relates to nutrition for infants, in particular infant formula, intended to be used as a sole source of nutrition.

BACKGROUND OF THE INVENTION

Human milk is the uncontested gold standard concerning infant nutrition. However, in some cases breastfeeding is inadequate or unsuccessful for medical reasons or because of a choice not to breastfeed. For such situations infant or follow on formulas have been developed. Commercial infant formulas are commonly used today to provide supplemental or sole source of nutrition early in life. These formulas comprise a range of nutrients to meet the nutritional needs of the growing infant, and typically include fat, carbohydrate, protein, vitamins, minerals, and other nutrients helpful for optimal infant growth and development. Commercial infant formulas are designed to mimic, as closely as possible, the composition and function of human milk.

Since long it has been appreciated that breastfed infants have a different weight gain pattern or trajectory compared to formula-fed infants. After the first week of life, in which breastfed infants initially tend to lose more weight than formula-fed infants and take slightly longer to regain their birth weight, the weight gain patterns are similar between breastfed and formula-fed infants for the first 4 months of life. Breastfed infants tend to have slightly higher weight at 3 months age (Andres et al, 2013, J Pediatrics 163: 49-54). After about 4 months of age, the rate of weight gain diverges markedly between breastfed and formula-fed infants. The difference in average weight at 12 months approximates up to 500-650 g (Dewey et al., 1993, Am J Clin Nutr 57: 140-145). Numerous studies performed in various regions from all over the world have reported that breastfed infants have a slower weight gain between 4 and 12 months of life in Western developed countries as well as in non-Western developing countries. Length gain tends to differ less between breastfed and formula-fed infants and as a result breastfed infants are leaner at 12 months of age (Dewey et al., 1993). Thus, in the art it has been indicated that the growth curve of infants fed with commercial infant formula differs from the growth curve of breastfed infants. Typically the infant formula has a growth accelerating effect in the first year of life, in particular from 4 months of age onwards, resulting in a higher weight at 12 months of age (Dewey et al., 1993; Dewey et al, 1992 Pediatrics 89:1035).

In the prior art in the field of infant formula for improving the growth trajectory to be more similar to the growth trajectory of breastfed infants, the focus is on infant formula with lower protein and/or lower caloric density. WO 2008/071667 discloses a nutritional composition for infants at risk of developing obesity later in life comprising a protein source, a lipid source and a carbohydrate source. The protein content is less than 1.8 g/100 kcal and the energy density is less than 650 kcal/litre. In WO 2010/070613 it is disclosed that a lower weight gain in the first week of life was observed when using a formula with a very low caloric content and low protein content based on volume. Koletzko et al, 2009, Am J Clin Nutr 89:1836-1845 disclose that using an isocaloric infant and follow on formula with a protein content of 1.77 and 2.1 g/100 kcal resulted in less weight gain than in the group of infants consuming an infant or follow on formula with a high protein concentration of 2.9 and 4.4 g/100 kcal. At 24 months, the weight-for-length z-score of infants in the lower protein formula group was lower than that of the high protein group and did not differ from that of the breastfed reference group. In WO 2015/078505 a lower weight gain is observed in the 3 to 6 months period when a formula is administered comprising a lower protein content than in the control. WO 2015/091789 focusses on oligosaccharide mixtures comprising N-acetylated oligosaccharide, galacto-oligosaccharide and/or sialylated oligosaccharide promoting a rate of growth which approximates to the rate of growth of a breast-fed infants. In WO 2013/153071 it is presented that formula is tested comprising sialic acid, cholesterol, sphingomyelin, and a lower caloric content and lower protein content compared to the control formula. No difference was observed in the growth up to 6 month when looking at age adjusted z-scores, when feeding these formulas and compared to breastfed infants. In Timby et al, 2014, Am J Clin Nutr 99:860-868 the 12 month data of a similar study show that both formula fed groups show statistically significant higher growth velocity than the breastfed reference group for weight and length. In WO 2009/051502 infant formula rich in a source of gangliosides are disclosed to increase or maintain a healthy growth. A postnatal increase in body weight was observed in rats receiving a gel enriched in gangliosides.

Human milk lipids have a distinct physical structure composed of large lipid globules with an average mode diameter of about 4 μm existing of a triglyceride core coated by a tri-layer of membranes, the milk fat globule membrane (MFGM). The diameter of lipid droplets in standard infant formula is about 0.3-0.5 μm due to the industrial processing procedures to achieve stable and reproducible end products, and is not surrounded by MFGM but mostly by proteins such as casein. Infant formula with lipid globules with an architecture more similar to the lipid globules in human milk have been described. WO 2015/065193 discloses nutritional compositions comprising specifically designed lipid globules for preterm infants, small for gestational age infants and infants with retarded growth due to physical or mental stress after birth, for promoting catch up growth and/or improved body composition. In WO 2012/173467 the use of specifically designed lipid component with optimal fatty acid profile, an enhanced portion of the palmitic acid residues at the sn-2 position and present as lipid globules with a certain size and/or coating is disclosed for an early in life diet for improving the development of a healthy body composition, in particular prevention of obesity, later in life.

SUMMARY OF THE INVENTION

The inventors compared the growth pattern or growth trajectory of 3 groups of healthy term infants during the first 12 months of life with each other and with the WHO Child Growth Standards of breastfed infants. One group was a non-randomised reference group of breastfed infants, one group received an experimental infant formula comprising a lipid component in the form of large lipid globules coated with phospholipids, and one group received a control infant formula without a lipid component in the form of large lipid globules coated with phospholipids, but in the form of standard lipid globules coated with protein. Both formulas were administered up to 17 weeks of life. The control and experimental milk formula were similar in caloric content, as well as in fat, carbohydrate and protein content.

The inventors surprisingly found that when analysing the growth trajectories for the whole study period up to 12 months of age in the per protocol (PP) population with a parametric growth curve (PGC), the group of infants receiving the experimental formula was not statistically different from the breastfed reference group, when looking at weight and body mass index (BMI) at 12 months of age. The group receiving control formula on the other hand showed a statistically significant higher weight and BMI at 12 months, when compared with the breastfed reference group. Furthermore the group receiving control formula showed a statistically significant higher BMI, when compared with the group fed with the experimental formula at 12 months.

In the control group, analysing the intention to treat (ITT) population, the mean weight-for-age z-score, weight-for-length z-score and BMI-for age z-score at 12 months of age were significantly higher compared to the WHO Child Growth Standards of breastfed infants. In the control group, analysing the intention to treat (ITT) population, the mean head circumference-for-age z-score, was significantly higher compared to the WHO Child Growth Standards of breastfed infants. The experimental group on the other hand was more similar to the breastfed reference group for all these z-scores as indicated by the overlapping confidence intervals and for both groups (experimental formula fed group and breastfed reference group) there was no indication for a difference from the WHO Child Growth Standards.

This indicates that feeding an infant formula with a similar caloric content and macro-ingredient content can have a different and beneficial effect on the growth pattern or growth trajectory early in life, rendering it advantageously more similar to the growth pattern or trajectory early in life of breastfed infants. This is due to the difference in which the way the lipid component is configured, namely in a way more resembling human milk lipid globules, by being larger in size and/or coated with phospholipids.

DETAILED DESCRIPTION OF THE INVENTION

The present invention thus concerns a method for promoting a postnatal growth trajectory or body development in an infant towards a growth trajectory or body development which is similar to the growth trajectory or body development observed in human milk fed infants, said method comprising administering a nutritional composition selected from an infant formula and a follow on formula to an infant, wherein the nutritional composition comprises 3 to 7 g lipid/100 kcal, 1.25 to 5 g protein/100 kcal and 6 to 18 g digestible carbohydrate/100 kcal and wherein the nutritional composition comprises lipid globules having
a) a mode diameter, based on volume of at least 1.0 μm and/or having a diameter of 2 to 12 μm in an amount of at least 45 volume % based on total lipid, and/or
b) on the surface at least partly a coating of phospholipids.

In one embodiment, a growth trajectory or body development which is similar to the growth trajectory or body development observed in human milk fed infants, is a growth trajectory or body development which is closer to the optimal growth trajectory or body development of the WHO Child Growth Standards of human milk fed infants. In the context of the present invention, the WHO Child Growth Standards of human milk fed infants refers to the WHO Child Growth Standards published in Acta Paediatrica, April 2006, volume 95, supplement 450.

In the context of the present invention 'similar' or 'closer' is compared to when a standard infant formula of follow on formula not comprising lipid globules having a) a mode diameter, based on volume of at least 1.0 μm and/or having a diameter of 2 to 12 μm in an amount of at least 45 volume % based on total lipid, and/or b) on the surface at least partly a coating of phospholipids is administered, more in particular when compared to standard infant formula of follow on formula comprising lipid globules of about 0.5 μm and that do not have a coating of phospholipids.

As an alternative to the 'promoting a postnatal growth trajectory or body development in an infant towards a growth trajectory or body development which is similar to the growth trajectory or body development observed in human milk fed infants', the present invention also concerns improving the postnatal growth trajectory or body development in an infant towards the growth trajectory or body development observed in human milk fed infants, preferably when compared to the growth trajectory or body development in infants fed infant formula of follow on formula comprising lipid globules of about 0.5 μm and that do not have a coating of phospholipids.

Thus in one embodiment, the present invention concerns a method for improving the postnatal growth trajectory or body development in an infant towards the growth trajectory or body development observed in human milk fed infants, preferably when compared to the growth trajectory or body development in infants fed infant formula of follow on formula comprising lipid globules of about 0.5 μm and that do not have a coating of phospholipids, wherein the nutritional composition comprises 3 to 7 g lipid/100 kcal, 1.25 to 5 g protein/100 kcal and 6 to 18 g digestible carbohydrate/100 kcal and wherein the nutritional composition comprises lipid globules having
a) a mode diameter, based on volume of at least 1.0 μm and/or having a diameter of 2 to 12 μm in an amount of at least 45 volume % based on total lipid, and/or
b) on the surface at least partly a coating of phospholipids.

Alternatively, the present invention concerns a method for promoting a postnatal growth trajectory or body development in an infant towards a growth trajectory or body development which is closer to the optimal growth trajectory or body development of the WHO Child Growth Standards of human milk fed infants, said method comprising administering a nutritional composition selected from an infant formula and a follow on formula to an infant, wherein the nutritional composition comprises 3 to 7 g lipid/100 kcal, 1.25 to 5 g protein/100 kcal and 6 to 18 g digestible carbohydrate/100 kcal and wherein the nutritional composition comprises lipid globules having
a) a mode diameter, based on volume of at least 1.0 μm and/or having a diameter of 2 to 12 μm in an amount of at least 45 volume % based on total lipid, and/or
b) on the surface at least partly a coating of phospholipids.

In some jurisdictions administering a nutritional composition to an infant is considered non-therapeutic. In those instances the invention can be worded as defined above by way of a method comprising administering a nutritional composition. For clarity, the method can also be defined as a non-therapeutic method for promoting a postnatal growth trajectory or body development in an infant as defined above. By definition, the words "non-therapeutic" exclude any therapeutic effect.

In some jurisdictions administering a nutritional composition to an infant is considered therapeutic per se. In this instances the invention can be worded as follows.

In one embodiment the invention concerns the use of lipid globules in the manufacture of a nutritional composition selected from an infant formula and a follow on formula for use in promoting a postnatal growth trajectory or body development in an infant towards a growth trajectory or body development which is similar to the growth trajectory or body development observed in human milk fed infants, wherein the nutrition composition comprises 3 to 7 g lipid/100 kcal, 1.25 to 5 g protein/100 kcal and 6 to 18 g digestible carbohydrate/100 kcal and the lipid globules have
a) a mode diameter, based on volume of at least 1.0 μm and/or having a diameter of 2 to 12 μm in an amount of at least 45 volume % based on total lipid, and/or
b) on the surface at least partly a coating of phospholipids.

In one embodiment the invention concerns the use of lipid globules in the manufacture of a nutritional composition selected from an infant formula and a follow on formula for use in improving the postnatal growth trajectory or body development in an infant towards the growth trajectory or body development observed in human milk fed infants, preferably when compared to the growth trajectory or body development in infants fed infant formula of follow on formula comprising lipid globules of about 0.5 μm and that do not have a coating of phospholipids, wherein the nutrition composition comprises 3 to 7 g lipid/100 kcal, 1.25 to 5 g protein/100 kcal and 6 to 18 g digestible carbohydrate/100 kcal and the lipid globules have
a) a mode diameter, based on volume of at least 1.0 μm and/or having a diameter of 2 to 12 μm in an amount of at least 45 volume % based on total lipid, and/or
b) on the surface at least partly a coating of phospholipids.

In one embodiment the invention concerns the use of lipid globules in the manufacture of a nutritional composition selected from an infant formula and a follow on formula for use in promoting a postnatal growth trajectory or body development in an infant towards a growth trajectory or body development which is closer to the optimal growth trajectory or body development of the WHO Child Growth Standards of human milk fed infants, wherein the nutrition composition comprises 3 to 7 g lipid/100 kcal, 1.25 to 5 g protein/100 kcal and 6 to 18 g digestible carbohydrate/100 kcal and the lipid globules have
a) a mode diameter, based on volume of at least 1.0 μm and/or having a diameter of 2 to 12 μm in an amount of at least 45 volume % based on total lipid, and/or
b) on the surface at least partly a coating of phospholipids.

The invention can also be worded as a nutritional composition selected from an infant formula and a follow on formula comprising 3 to 7 g lipid/100 kcal, 1.25 to 5 g protein/100 kcal and 6 to 18 g digestible carbohydrate/100 kcal and comprising lipid globules having
a) a mode diameter, based on volume of at least 1.0 μm and/or having a diameter of 2 to 12 μm in an amount of at least 45 volume % based on total lipid, and/or
b) on the surface at least partly a coating of phospholipids for use in promoting a postnatal growth trajectory or body development in an infant towards a growth trajectory or body development which is similar to the growth trajectory or body development observed in human milk fed infants.

The invention can also be worded as a nutritional composition selected from an infant formula and a follow on formula comprising 3 to 7 g lipid/100 kcal, 1.25 to 5 g protein/100 kcal and 6 to 18 g digestible carbohydrate/100 kcal and comprising lipid globules having
a) a mode diameter, based on volume of at least 1.0 μm and/or having a diameter of 2 to 12 μm in an amount of at least 45 volume % based on total lipid, and/or
b) on the surface at least partly a coating of phospholipids for use in improving the postnatal growth trajectory or body development in an infant towards the growth trajectory or body development observed in human milk fed infants, preferably when compared to the growth trajectory or body development in infants fed infant formula of follow on formula comprising lipid globules of about 0.5 μm and that do not have a coating of phospholipids.

The invention can also be worded as a nutritional composition selected from an infant formula and a follow on formula comprising 3 to 7 g lipid/100 kcal, 1.25 to 5 g protein/100 kcal and 6 to 18 g digestible carbohydrate/100 kcal and comprising lipid globules having
a) a mode diameter, based on volume of at least 1.0 μm and/or having a diameter of 2 to 12 μm in an amount of at least 45 volume % based on total lipid, and/or
b) on the surface at least partly a coating of phospholipids for use in promoting a postnatal growth trajectory or body development in an infant towards a growth trajectory or body development which is closer to the optimal growth trajectory or body development of the WHO Child Growth Standards of human milk fed infants.

In a preferred embodiment of the method, use or composition for use according to the invention, the growth trajectory or body development is the growth trajectory or body development of the first 12 months of life of the infant.

In a preferred embodiment of the method, use or composition for use according to the invention, at 12 months the infant has a weight and/or BMI and/or weight for length that is approximate to the weight and/or BMI and/or weight for length at 12 months of human milk fed infants. In a preferred embodiment of the method, use or composition for use according to the invention, at 12 months the infant has a weight and/or BMI and/or weight for length that is approximate to the weight and/or BMI and/or weight for length at 12 months according to the WHO Child Growth Standards of human milk fed infants. In the context of the present invention, approximate means that it is statistically not different.

In another embodiment of the method, use or composition for use according to the invention, at 12 months the infant has a head circumference that is approximate to the head circumference at 12 months of human milk fed infants. In a preferred embodiment of the method, use or composition for use according to the invention, at 12 months the infant has a head circumference that is approximate to the head circumference at 12 months according to the WHO Child Growth Standards of human milk fed infants. In the context of the present invention, approximate means that it is statistically not different.

In another embodiment of the method, use or composition for use according to the invention, at 12 months the infant has a skinfold thickness, preferably subscapular skinfold thickness or triceps skinfold thickness or both, that is approximate to the skinfold thickness at 12 months of human milk fed infants. In a preferred embodiment of the method, use or composition for use according to the invention, at 12 months the infant has a subscapular skinfold thickness or triceps skinfold thickness or both, that is approximate to the subscapular skinfold thickness or triceps skinfold thickness at 12 months according to the WHO Child Growth Standards of human milk fed infants. In the context of the present invention, approximate means that it is statistically not different.

In one embodiment, the present invention relates to a method for i) promoting a balanced growth trajectory or body development in an infant and/or ii) preventing or reducing the risk of an unbalanced growth trajectory or body development in an infant, said method comprising administering a nutritional composition selected from an infant formula and a follow on formula to an infant, wherein the nutritional composition comprises 3 to 7 g lipid/100 kcal, 1.25 to 5 g protein/100 kcal and 6 to 18 g digestible carbohydrate/100 kcal and wherein the nutritional composition comprises lipid globules having
a) a mode diameter, based on volume of at least 1.0 μm and/or having a diameter of 2 to 12 μm in an amount of at least 45 volume % based on total lipid, and/or
b) on the surface at least partly a coating of phospholipids.

The invention can also be worded as the use of lipid globules in the manufacture of a nutritional composition selected from an infant formula and a follow on formula for use in i) promoting a balanced growth trajectory or body development in an infant and/or ii) preventing or reducing the risk of an unbalanced growth trajectory or body development in an infant, wherein the nutrition composition comprises 3 to 7 g lipid/100 kcal, 1.25 to 5 g protein/100 kcal and 6 to 18 g digestible carbohydrate/100 kcal and the lipid globules have
a) a mode diameter, based on volume of at least 1.0 μm and/or having a diameter of 2 to 12 μm in an amount of at least 45 volume % based on total lipid, and/or
b) on the surface at least partly a coating of phospholipids.

The invention can also be worded as a nutritional composition selected from an infant formula and a follow on formula comprising 3 to 7 g lipid/100 kcal, 1.25 to 5 g protein/100 kcal and 6 to 18 g digestible carbohydrate/100 kcal and comprising lipid globules having
a) a mode diameter, based on volume of at least 1.0 μm and/or having a diameter of 2 to 12 μm in an amount of at least 45 volume % based on total lipid, and/or
b) on the surface at least partly a coating of phospholipids for use in i) promoting a balanced growth trajectory or body development in an infant and/or
ii) preventing or reducing the risk of an unbalanced growth trajectory or body development in an infant.

Preferably a balanced growth trajectory or body development compares or is similar to a growth trajectory or body development observed in human milk fed infants. In one embodiment a balanced growth trajectory or body development is closer to the optimal growth trajectory or body development of the WHO Child Growth Standards of human milk fed infants.

In the context of the present invention, the nutritional composition is not human milk. Also in the context of the present invention, the nutritional composition is not cow's milk, in particular cow's milk that is not homogenised.

Growth

The present invention concerns promoting a postnatal growth trajectory or body development in an infant towards a growth trajectory or body development which is similar to the growth trajectory or body development observed in human milk fed infants. Synonyms for growth trajectory are growth pattern and growth for age. In the context of the present invention, growth trajectory includes weight pattern, i.e. weight for age, weight-for-length pattern, i.e. weight-for-length-for age and body mass index (BMI) pattern, i.e. BMI for age. In one embodiment, growth trajectory also includes head circumference for age. In one embodiment, growth trajectory also includes subscapular skinfold-for-age or triceps skinfold-for-age or both.

The World Health Organization (WHO) released a new international growth standard statistical distribution in 2006, which describes the growth of children aged 0 to 59 months living in environments believed to support what WHO researchers view as optimal growth of children in six countries throughout the world, including the U.S. The distribution shows how infants and young children grow under these conditions, rather than how they grow in environments that may not support optimal growth. The WHO standards establish growth of the breastfed infant as the norm for growth. The WHO charts reflect growth patterns among children who were predominantly breastfed for at least 4 months and were still breastfeeding at 12 months. The WHO standards provide a better description of physiological growth in infancy. The WHO growth charts are standards in the sense that they identify how children should grow when provided optimal conditions. The WHO standards are based on a high-quality study designed explicitly for creating growth charts. The WHO standards were constructed using longitudinal length and weight data measured at frequent intervals. Also z scores are given. The z score or standard score is the number of standard deviations that an observation or datum is above the mean (for a positive z score) or below the mean (for a negative z score).

Lipid Globule Size

According to the present invention, the nutritional composition comprises lipid globules. When in liquid form these lipid globules are emulsified in the aqueous phase. Alternatively the lipid globules are present in a powder and the powder is suitable for reconstitution with water or another food grade aqueous phase, preferably to provide a ready to drink formula. The lipid globules comprise a core and a surface. The core preferably comprises vegetable fat and preferably comprises at least 90 wt. % triglycerides and more preferably essentially consists of triglycerides. Not all vegetable lipids that are present in the composition need necessarily be comprised in the core of lipid globules, but preferably a major part is, preferably more than 50% wt. %, more preferably more than 70 wt. %, even more preferably more than 85 wt. %, even more preferably more than 95 wt. %, most preferably more than 98 wt. % of the vegetable lipids that are present in the composition are comprised in the core of lipid globules. In one embodiment the core of the lipid globules comprises at least 40 wt. % triglycerides of vegetable origin, more preferably at least 50 wt. %, even more preferably at least 70 wt. % triglycerides of vegetable origin, more preferably the core of the lipid globules comprises at least 85 wt. %, more preferably at least 95 wt. % triglycerides of vegetable origin. The lipid globules in the nutritional composition in the method or use of the present invention have a volume-weighted mode diameter above 1.0 μm, preferably above 3.0 μm, more preferably 4.0 μm or above, preferably between 1.0 and 10 μm, more preferably between 2.0 and 8.0 μm, even more preferably between 3.0 and 8.0 μm, most preferably between 4.0 μm and 8.0 μm. Preferably in addition the size distribution is in such a way that at least 45 volume %, preferably at least 55 volume %, even more preferably at least 65 volume %, even more preferably at least 75 volume % has a diameter between 2 and 12 μm. More preferably at least 45 volume %, preferably at least 55 volume %, even more preferably at least 65 volume %, even more preferably at least 75 volume % has a diameter between 2 and 10 µm. Even more preferably at least 45 volume %, preferably at least 55 volume %, even more preferably at least 65 volume %, even more preferably at least 75 volume % has a diameter between 4 and 10 µm. Preferably less than 5 volume % has a diameter above 12 um.

Standard infant formulae or follow on formulae have lipid globules with mode diameter below 0.5 µm. It was found that large lipid globules promote a growth trajectory or body development that is more similar to that of human milk fed infants. The percentage of lipid globules is based on volume of total lipid. The mode diameter relates to the diameter which is the most present based on volume of total lipid, or the peak value in a graphic representation, having on the X-as the diameter and on the Y-as the volume (%).

The volume of the lipid globule and its size distribution can suitably be determined using a particle size analyzer such as a Mastersizer (Malvern Instruments, Malvern, UK), for example by the method described in Michalski et al, 2001, Lait 81: 787-796.

Coating with Phospholipids

According to the present invention, the nutritional composition preferably comprises polar lipids. Polar lipids are amphipathic of nature and include glycerophospholipids, glycosphingolipids, sphingomyelin and/or cholesterol. More preferably the nutritional composition comprises phospholipids (the sum of glycerophospholipids and sphingomyelin). Polar lipids in the present invention relate to the sum of glycerophospholipids, glycosphingolipids, sphingomyelin and cholesterol. Polar lipids, more preferably phospholipids, are preferably present as a coating on the surface of the lipid globule. By 'coating' is meant that the outer surface layer of the lipid globule comprises polar lipids, whereas these polar lipids are virtually absent in the core of the lipid globule. The presence of polar lipids, in particular, phospholipids as a coating or outer layer of the lipid globule in the diet administered was found to advantageously promote a growth trajectory or body development that is more similar to that of human milk fed infants. Thus in one embodiment the coating preferably comprises phospholipids and/or polar lipids. Not all phospholipids and/or polar lipids that are present in the composition need necessarily be comprised in the coating, but preferably a major part is. Preferably more than 30 wt. %, more preferably more than 50 wt. %, more preferably more than 70 wt. %, even more preferably more than 85 wt. %, most preferably more than 95 wt. % of the phospholipids and/or polar lipids that are present in the composition are comprised in the coating of lipid globules. In a preferred embodiment the nutritional composition in the method or use according to the present invention comprises phospholipids, preferably the nutritional composition comprises at least 0.5 wt. % phospholipids based on total lipid. Yet further preferably the phospholipids comprise at least 15 wt. % sphingomyelin based on total phospholipids.

In one embodiment, in the nutritional composition in the method or the use according to the invention, the lipid globules have a volume mode diameter of 1.0 µm or above, and are at least partly coated on the surface with phospholipids. Preferably the amount of phospholipids present in the nutritional composition ranges from 0.5 to 20 wt. % phospholipids based on total lipid. A combination of large lipid globule size and coating further promotes a growth trajectory or body development that is more similar to that of human milk fed infants, when compared to small and not phospholipid coated lipid globules.

According to the present invention, the nutritional composition preferably comprises glycerophospholipids. Glycerophospholipids are a class of lipids formed from fatty acids esterified at the hydroxyl groups on carbon-1 and carbon-2 of the backbone glycerol moiety and a negatively-charged phosphate group attached to carbon-3 of the glycerol via an ester bond, and optionally a choline group (in case of phosphatidylcholine, PC), a serine group (in case of phosphatidylserine, PS), an ethanolamine group (in case of phosphatidylethanolamine, PE), an inositol group (in case of phosphatidylinositol, PI) or a glycerol group (in case of phosphatidylglycerol, PG) attached to the phosphate group. Lysophospholipids are a class of phospholipids with one fatty acyl chain. Preferably the present composition contains PC, PS, PI and/or PE, more preferably at least PC.

Preferably the nutritional composition comprises sphingomyelin. Sphingomyelins have a phosphorylcholine or phosphorylethanolamine molecule esterified to the 1-hydroxy group of a ceramide. They are classified as phospholipid as well as sphingolipid, but are not classified as a glycerophospholipid nor as a glycosphingolipid. Preferably the nutritional composition comprises 0.05 to 10 wt. % sphingomyelin based on total lipid, more preferably 0.1 to 5 wt. %, even more preferably 0.2 to 2 wt. %.

According to the present invention, the nutritional composition preferably comprises glycosphingolipids. The term glycosphingolipids as in the present invention particularly refers to glycolipids with an amino alcohol sphingosine. The sphingosine backbone is O-linked to a charged headgroup such as ethanolamine, serine or choline backbone. The backbone is also amide linked to a fatty acyl group. Glycosphingolipids are ceramides with one or more sugar residues joined in a β-glycosidic linkage at the 1-hydroxyl position. Preferably the nutritional composition contains gangliosides, more preferably at least one ganglioside selected from the group consisting of GM3 and GD3.

Sphingolipids are in the present invention defined as the sum of sphingomyelin and glycosphingolipids. Phospholipids are in the present invention defined as the sum of sphingomyelin and glycerophospholipids. Preferably the phospholipids are derived from milk lipids. Preferably the weight ratio of phospholipids:glycosphingolipids is from 2:1 to 10:1, more preferably 2:1 to 5:1.

According to the present invention, the nutritional composition preferably comprises phospholipids. Preferably the nutritional composition comprises 0.5 to 20 wt. % phospholipids based on total lipid, more preferably 0.5 to 10 wt. %, more preferably 1 to 10 wt. %, even more preferably 2 to 10 wt. % even more preferably 3 to 8 wt. % phospholipids based on total lipid. Preferably the nutritional composition comprises 0.1 to 10 wt. % glycosphingolipids based on total lipid, more preferably 0.5 to 5 wt. %, even more preferably 2 to 4 wt. %. Preferably the nutritional composition comprises 0.5 to 10 wt. % (glycosphingolipids plus phospholipids) based on total lipid, more preferably 1.0 to 10 wt. % (glycosphingolipids plus phospholipids) based on total lipid. In one embodiment, the nutritional composition for the method or use according to the invention comprises phospholipids, wherein the phospholipids comprise glycolipids, and/or are derived from or form part of the milk fat globule membrane (MFGM), preferably cow's milk MFGM.

According to the present invention, the nutritional composition preferably comprises cholesterol. The nutritional composition preferably comprises at least 0.005 wt. % cholesterol based on total lipid, more preferably at least 0.01 wt. %, more preferably at least 0.02 wt. %, more preferably at least 0.05 wt. %, even more preferably at least 0.1 wt. %. Preferably the amount of cholesterol does not exceed 10 wt.

% based on total lipid, more preferably does not exceed 5 wt. %, even more preferably does not exceed 1 wt. % of total lipid.

According to the present invention, the nutritional composition preferably comprises 0.6 to 25 wt. % polar lipids based on total lipid, wherein the polar lipids are the sum of phospholipids, glycosphingolipids, and cholesterol, more preferably 0.6 to 12 wt. %, more preferably 1 to 10 wt. %, even more preferably 2 to 10 wt. %, even more preferably 3.0 to 10 wt. % polar lipids based on total lipid, wherein the polar lipids are the sum of phospholipids, glycosphingolipids, and cholesterol.

Preferred sources for providing the phospholipids, glycosphingolipids and/or cholesterol are egg lipids, milk fat, buttermilk fat and butter serum fat, such as beta serum fat. A preferred source for phospholipids, particularly PC, is soy lecithin and/or sunflower lecithin. According to the present invention, the nutritional composition preferably comprises phospholipids derived from mammalian milk. Preferably the nutritional composition comprises phospholipids and glycosphingolipids derived from milk. Preferably also cholesterol is obtained from milk. Preferably the polar lipids, in particular phospholipids, are derived from milk. Polar lipids, in particular phospholipids, derived from milk include the polar lipids, in particular phospholipids, isolated from milk lipid, cream lipid, cream serum lipid, butter serum lipid, beta serum lipid, whey lipid, cheese lipid and/or buttermilk lipid. The buttermilk lipid is typically obtained during the manufacture of buttermilk. The butter serum lipid or beta serum lipid is typically obtained during the manufacture of anhydrous milk fat from butter. Preferably the phospholipids, glycosphingolipids and/or cholesterol are obtained from milk cream. The nutritional composition preferably comprises phospholipids, glycosphingolipids and/or cholesterol from milk of cows, mares, sheep, goats, buffalos, horses and camels. It is most preferred to use a lipid extract isolated from cow's milk. The use of polar lipids from milk fat advantageously comprises the polar lipids from milk fat globule membranes, which are more reminiscent to the situation in human milk. Polar lipids, in particular phospholipids, derived from fat milk advantageously promote a growth trajectory more effectively than polar lipids from other sources. The polar lipids, in particular phospholipids, are located on the surface of the lipid globule, i.e. as a coating or outer layer. It was found that when the polar lipids or phospholipids are present in the coating of the lipid globule they are more effective than when they are dry blended into the powdered product, i.e. present as ingredient as such. A suitable way to determine whether the polar lipids are located on the surface of the lipid globules is laser scanning microscopy. The concomitant use of polar lipids in particular phospholipids, derived from domestic animals milk and triglycerides derived from vegetable lipids therefore enables to manufacture coated lipid globules with a coating more similar to human milk, while at the same time providing an optimal fatty acid profile. Suitable commercially available sources for milk polar lipids are BAEF, SM2, SM3 and SM4 powder of Corman, Salibra of Glanbia, and LacProdan MFGM-10 or PL20 from Arla. Preferably the source of milk polar lipids comprises at least 4 wt. % phospholipids based on total lipid, more preferably 7 to 75 wt. %, most preferably 20 to 70 wt. % phospholipids based on total lipid. Preferably the weight ratio phospholipids to protein is above 0.10, more preferably above 0.20, even more preferably above 0.3. Preferably at least 25 wt. %, more preferably at least 40 wt. %, most preferably at least 75 wt. % of the polar lipids, in particular phospholipids, is derived from milk polar lipids.

Methods for obtaining lipid globules with an increased size and/or coating with phospholipids are disclosed in WO 2010/0027258, WO 2010/0027259 and WO 2013/135738.

Preferably in the nutritional composition in the method or the use according to the invention, the lipid globules are both increased in size, compared to the size in standard infant formula, as well as at least partly coated with phospholipids. Thus in one embodiment in the nutritional composition in the method or the use according to the invention, the lipid globules have a) a mode diameter, based on volume of at least 1.0 μm and/or a diameter of 2 to 12 μm in an amount of at least 45 volume % based on total lipid, and b) on the surface at least partly a layer of phospholipids.

All preferred embodiments described for lipid globule size and for coating with phospholipids described above apply to the combination of both features as well.

Infant Formula and Follow on Formula

The nutritional composition to be administered in the method or use according to the present invention is selected from an infant formula and a follow on formula. This means that the present nutrition composition is not human milk. Alternatively the term "formula" means that it concerns a composition that is artificially made or in other words that it is synthetic. Hence in one embodiment the nutritional composition is selected from an artificial infant formula and an artificial follow on formula or a synthetic infant formula and a synthetic follow on formula. In the present context, infant formula refers to nutritional compositions, artificially made, intended for infants of 0 to about 4 to 6 months of age and are intended as a substitute for human milk. Typically infant formulae are suitable to be used as sole source of nutrition. Such formulae are also known as starter formula. Formula for infants starting with at 4 to 6 months of life to 12 months of life are intended to be supplementary feedings to infants that start weaning on other foods. Such formulae are also known as follow on formulae. Infant and follow on formulae are subject to strict regulations, for example for the EU Commission Directive 2006/141/EC.

The nutritional composition comprises 3 to 7 g lipid/100 kcal, preferably 4 to 6 g lipid/100 kcal, more preferably 4.5 to 5.5 g lipid/100 kcal, 1.25 to 5 g protein/100 kcal, preferably 1.35 to 4 g protein/100 kcal, more preferably 1.5 to 3 g protein/100 kcal, more preferably 1.25 to 2.5 g protein/100 kcal, more preferably 1.25 to 2.25 g/100 kcal, even more preferably 1.25 to 2.1 g protein/100 kcal and 6 to 18 g digestible carbohydrate/100 kcal, preferably 8 to 16 g digestible carbohydrate/100 kcal, more preferably 10 to 15 g digestible carbohydrate/100 kcal.

Lipid

Herein LA refers to linoleic acid and/or acyl chain (18:2 n6); ALA refers to α-linolenic acid and/or acyl chain (18:3 n3); PUFA refers to polyunsaturated fatty acids and/or acyl chains; MUFA refers to monounsaturated fatty acids and/or acyl chains; LC-PUFA refers to long chain polyunsaturated fatty acids and/or acyl chains comprising at least 20 carbon atoms in the fatty acyl chain and with 2 or more unsaturated bonds; DHA refers to docosahexaenoic acid and/or acyl chain (22:6, n3); EPA refers to eicosapentaenoic acid and/or acyl chain (20:5 n3); ARA refers to arachidonic acid and/or acyl chain (20:4 n6); DPA refers to docosapentaenoic acid and/or acyl chain (22:5 n3). PA relates to palmitic acid and/or acyl chains (C16:0). Medium chain fatty acids (MCFAs) refer to fatty acids and/or acyl chains with a chain length of 6, 8 or 10 carbon atoms.

The lipid in the nutritional composition to be administered in the method or use according to the present invention preferably comprises vegetable lipids. The lipid that is present in the nutritional composition in the method or use according to the invention preferably comprises PUFAs, more preferably LC-PUFAs, as LC-PUFAs further improve the growth patterns and body development. The nutritional composition preferably comprises 5 to 35 wt. % PUFA, more preferably 10 to 30 wt. % PUFA, most preferably 15 to-20 wt. % PUFA, based on total lipid. In one embodiment the lipid in the nutritional composition for the method or use according to the invention comprises at least 10 wt. % polyunsaturated fatty acid based on total fatty acids. It is also preferred that the nutritional composition comprises MUFAs, preferably 10 to 80 wt. % MUFA, more preferably 20 to 70 wt. % MUFA, most preferably 35 to 55 wt. % MUFA, based on total lipid.

LA preferably is present in a sufficient amount in order to promote a healthy growth and development, yet in an amount as low as possible to prevent occurrence of unbalance in growth or body development. The nutritional composition therefore preferably comprises less than 20 wt. % LA based on total lipid, preferably 5 to 16 wt. %, more preferably 10 to 14.5 wt. %. Preferably, the nutritional composition comprises at least 5 wt. % LA based on total lipid. Per 100 kcal, the nutritional composition preferably comprises 350-1400 mg LA. Preferably, ALA is present in a sufficient amount to promote a healthy growth and development of the infant. The nutritional composition therefore preferably comprises at least 1.0 wt. % ALA based on total lipid. Preferably the nutritional composition comprises at least 1.5 wt. % ALA based on total lipid, more preferably at least 2.0 wt. %. Preferably the nutritional composition comprises less than 12.5 wt. % ALA, more preferably less than 10.0 wt. %, most preferably less than 5.0 wt. %. Preferably the nutritional composition comprises a weight ratio of LA/ALA from 2 to 20, more preferably from 3 to 16, more preferably from 4 to 14, more preferably from 5 to 12.

Preferably the nutritional composition comprises less than 10 wt. % short chain fatty acids based on total fatty acids, preferably less than 8 wt. %, preferably less than 6 wt. %, preferably less than 5 wt. %. Preferably the nutritional composition comprises at least 0.5 wt. % short chain fatty acids based on total fatty acids, preferably at least 0.6 wt. %, less than 8 wt. %, preferably at least 0.9 wt. %, more preferably at least 1.2 wt. %, more preferably at least 2.0 wt. %. Short chain fatty acids are fatty acids with an acyl chain of 2 to 6 carbon atoms. Preferably the nutritional composition comprises less than 10 wt. % butyric acid (acyl chain of 4 carbon atoms) based on total fatty acids, preferably less than 8 wt. %, preferably less than 6 wt. %, preferably less than 5 wt. %, preferably less than 4 wt. %. Preferably the nutritional composition comprises at least 0.5 wt. % butyric acid based on total fatty acids, preferably at least 0.6 wt. %, preferably at least 0.9 wt. %, more preferably at least 1.2 wt. %. The nutritional composition preferably comprises at least 3 wt. % MCFA based on total fatty acids, more preferably at least 10 wt. %, even more preferably 15 wt. %. The present composition advantageously comprises less than 50 wt. % MCFA based on total fatty acids, more preferably less than 30 wt. %, even more preferably less than 20 wt. %.

According to the present invention, the nutritional composition preferably comprises LC-PUFA, more preferably n-3 LC-PUFA, since n-3 LC-PUFA promote an advantageous growth trajectory. More preferably, the nutritional composition comprises EPA, DPA and/or DHA, even more preferably DHA. Since a low concentration of DHA, DPA and/or EPA is already effective and normal growth and development are important, the content of n-3 LC-PUFA in the nutritional composition, more preferably DHA, preferably does not exceed 15 wt. % of the total fatty acid content, preferably does not exceed 10 wt. %, even more preferably does not exceed 5 wt. %. Preferably the nutritional composition comprises at least 0.15 wt. %, preferably at least 0.35 wt. %, more preferably at least 0.75 wt. %, n-3 LC-PUFA, more preferably DHA, of the total fatty acid content. In one embodiment, the present composition comprises at least 0.15 wt. % n-3 LC-PUFA based on total fatty acids selected from the group consisting of DHA, EPA, and DPA, more preferably DHA.

As the group of n-6 fatty acids, especially arachidonic acid (ARA) and LA as its precursor, counteracts the group of n-3 fatty acids, especially DHA and EPA and ALA as their precursor, the nutritional composition comprises relatively low amounts of ARA. The n-6 LC-PUFA, more preferably ARA, content preferably does not exceed 5 wt. %, more preferably does not exceed 2.0 wt. %, more preferably does not exceed 0.75 wt. %, even more preferably does not exceed 0.5 wt. %, based on total fatty acids. As the presence of ARA is not necessary for promoting a growth trajectory of body development similar to that of human milk fed infants, ARA may also be absent.

Palmitic Acid at Sn-2 Position of Triglyceride

The lipid in the nutritional composition to be administered in the method or use according to the present invention comprises triglycerides. Triglycerides comprise a glyceride molecule to which, via ester bonds, three fatty acid residues are attached, which may be the same or different, and which are generally chosen from saturated and unsaturated fatty acids containing 6 to 26 carbon atoms, including but not limited to LA, ALA, oleic acid (C18:1), PA and/or stearic acid (C18:0). Such fatty acid triglycerides may differ in the fatty acid residues that are present and/or in the respective position(s) of the fatty acid residues, e.g. in the sn-1, -2 and/or -3 position. Preferably the triglycerides used in the nutritional composition are chosen such that the amount of PA residues that are present in the triglycerides are 10 wt. % or more based on total fatty acid present in the triglycerides, preferably more than 15 wt. %. Thus in one embodiment in the nutritional composition in the method or use according to the invention, the lipid comprises triglycerides that comprise at least 10 wt. % palmitic acid based on total fatty acids, and wherein at least 15% of the palmitic acid is present at the sn-2 position of the triglycerides. Preferably the amount of PA residues that are present in the triglycerides are below 30 wt. %, more preferably between 16 and 24%. Preferably the triglycerides used in the nutritional composition are chosen such that of the total PA residues present in the triglyceride at least 15%, preferably at least 20%, more preferably at least 30%, even more preferably at least 35%, and most preferably at least 40% are in the sn-2 or beta position of the triglyceride.

Suitable triglycerides for the nutritional composition in the method or use according to the invention are commercially available, e.g. from Loders Croklaan under the name Betapol™ and/or can be prepared in a manner known per se, for instance as described in EP 0 698 078 and/or EP 0 758 846. Another suitable source is InFat™ of Enzymotec. In case these lipids are obtained by trans- or interesterification of vegetable triglycerides, these sources are in the context of the present invention regarded as vegetable lipids. Preferably the amount of the triglyceride with increased amount of palmitic acid residues on the sn-2 position of a trygliceride molecule that is comprised in the lipid fraction of the composition that is to be administered according to the present method or use, is between 10 and 100 wt. %, preferably between 20 and 100 wt. %, more preferably between 20 and 80 wt. %, even more preferably between 50 and 80 wt. %.

A preferred source for triglycerides having palmitic acid at the sn-2 or beta position of the triglyceride is non human animal fat, more preferably non human mammalian milk fat, even more preferably cow's milk fat. Preferably non human mammalian milk fat, in particular cow's milk fat, is preferably used in the form of anhydrous milk fat or butter oil. Preferably the source of the milk fat is in a homogenous fat phase, such as butter oil or anhydrous milk fat, and not in the form of oil in water emulsion such as cream, since the lipid globules of the present nutritional composition can be more easily prepared when in a homogenous fat phase.

Preferably the amount of milk fat is between 10 and 100 wt. % based on total lipid, preferably between 10 and 80 wt. % based on total lipid, more preferably between 10 and 70 wt. %, more preferably between 20 and 80 wt. %, more preferably between 15 to 60 wt. %, more preferably between 20 and 60 wt. %, even more preferably between 25 and 50 wt. % based on total lipid.

Improved promotion of growth trajectory and/or body development similar to that of human milk fed infants was observed when such lipid component with increased amounts of palmitic acid located at the sn-2 position of triglyceride molecules was applied.

Protein

The nutritional composition comprises proteins, preferably in the amounts specified above. The source of the protein should be selected in such a way that the minimum requirements for essential amino acid content are met and satisfactory growth is ensured. Hence protein sources based on cows' milk proteins such as whey, casein and mixtures thereof and proteins based on soy, potato or pea are preferred. In case whey proteins are used, the protein source is preferably based on acid whey or sweet whey, whey protein isolate or mixtures thereof and may include α-lactalbumin and β-lactoglobulin. More preferably, the protein source is based on acid whey or sweet whey from which caseino-glyco-macropeptide (CGMP) has been removed. Preferably the composition comprises at least 3 wt. % casein based on dry weight. Preferably the casein is intact and/or non-hydrolyzed. For the present invention protein includes peptides and free amino acids.

Digestible Carbohydrates

The nutritional composition comprises digestible carbohydrate, preferably in the amounts specified above. Preferred digestible carbohydrate sources are lactose, glucose, sucrose, fructose, galactose, maltose, starch and maltodextrin. Lactose is the main digestible carbohydrate present in human milk. Lactose advantageously has a low glycemic index. The nutritional composition preferably comprises lactose. The nutritional composition preferably comprises digestible carbohydrate, wherein at least 35 wt. %, more preferably at least 50 wt. %, more preferably at least 75 wt. %, even more preferably at least 90 wt. %, most preferably at least 95 wt. % of the digestible carbohydrate is lactose. Based on dry weight the present composition preferably comprises at least 25 wt. % lactose, preferably at least 40 wt. %.

Non Digestible Carbohydrates

In one embodiment the nutritional composition comprises non-digestible oligosaccharides. Preferably the nutritional composition comprises non-digestible oligosaccharides with a degree of polymerization (DP) between 2 and 250, more preferably 3 and 60.

Preferably the present composition comprises fructo-oligosaccharides, inulin and/or galacto-oligosaccharides, more preferably galacto-oligosaccharides, most preferably trans-galacto-oligosaccharides. In a preferred embodiment the composition comprises a mixture of transgalacto-oligosaccharides and fructo-oligosaccharides or inulin. Suitable non-digestible oligosaccharides are for example Vivinal GOS (FrieslandCampina DOMO), Raftilin HP or Raftilose (Orafti).

Preferably, the nutritional composition comprises of 80 mg to 2 g non-digestible oligosaccharides per 100 ml, more preferably 150 mg to 1.50 g, even more preferably 300 mg to 1 g per 100 ml. Based on dry weight, the nutritional composition preferably comprises 0.25 wt. % to 20 wt. %, more preferably 0.5 wt. % to 10 wt. %, even more preferably 1.5 wt. % to 7.5 wt. %.

Application

In the method or use according to the present invention, a nutritional composition is administered to an infant or is used in an infant. In the context of the present invention an infant has an age up to 12 months. Preferably the nutritional composition is administered to or is used in a term infant. A term infant means an infant born art a gestational age of 37 to 42 weeks. Preferably the nutritional composition is administered to or is used in a healthy infant. Preferably, the nutritional composition is administered to a male infant. Although the effect of the nutritional composition of the invention on postnatal growth trajectories and body development was observed both in female and male infants, the effect was the largest in male infants. Preferably the nutritional composition is used at least during the first 2 months of life, preferably at least during the first 3 months of life of the infant, more preferably at least during the first 4 months of life of the infant. Preferably the nutritional composition is administered to an infant with an age below 6 months, more preferably below 4 months of age.

According to the present invention, a postnatal growth trajectory or body development in an infant towards a growth trajectory or body development which is similar to the growth trajectory or body development observed in human milk fed infants is promoted. Alternatively according to the present invention, a postnatal growth trajectory or body development in an infant towards a growth trajectory or body development which is closer to the optimal growth trajectory or body development of the WHO Child Growth Standards of human milk fed infants is promoted.

As an alternative to the 'promoting a postnatal growth trajectory or body development in an infant towards a growth trajectory or body development which is similar to the growth trajectory or body development observed in human milk fed infants', the present invention also concerns improving the postnatal growth trajectory or body development towards the growth trajectory or body development observed in human milk fed infants, preferably when compared to the growth trajectory or body development in infants fed infant formula of follow on formula comprising lipid globules of about 0.5 μm and that do not have a coating of phospholipids.

Preferably the growth trajectory or body development is selected from the group consisting of the trajectory or development for body weight, weight for length and/or body mass index (BMI). In a preferred embodiment, the growth trajectory or body development is the growth trajectory or body development of the first 12 months of life of the infant.

Preferably at 12 months the infant has a weight and/or BMI and/or weight for length that is approximate to the weight and/or BMI and/or weight for length at 12 months of human milk fed infants. Preferably at 12 months the infant has a weight and/or BMI and/or weight for length that is approximate to the weight and/or BMI and/or weight for length at 12 months according to the WHO Child Growth Standards of human milk fed infants.

Preferably the growth trajectory or body development is that for head circumference. In a preferred embodiment, the growth trajectory or body development is the growth trajectory or body development of the first 12 months of life of the infant. Preferably at 12 months the infant has a head circumference that is approximate to the head circumference at 12 months of human milk fed infants. Preferably at 12 months the infant has a head circumference that is approximate to the head circumference at 12 months according to the WHO Child Growth Standards of human milk fed infants.

Preferably the growth trajectory or body development is that for skinfold thickness, preferably that for subscapular skinfold thickness and/or triceps skinfold thickness. In a preferred embodiment, the growth trajectory or body development is the growth trajectory or body development of the first 12 months of life of the infant. Preferably at 12 months the infant has a skinfold thickness, preferably subscapular skinfold thickness and/or triceps skinfold thickness, that is approximate to the skinfold thickness at 12 months of human milk fed infants. Preferably at 12 months the infant has a subscapular skinfold thickness and/or triceps skinfold thickness that is approximate to the subscapular skinfold thickness and/or triceps skinfold thickness at 12 months according to the WHO Child Growth Standards of human milk fed infants.

In one embodiment according to the present invention i) a balanced growth trajectory or body development in an infant is promoted and/or an unbalanced growth trajectory or body development in an infant is prevented or the risk thereof is reduced.

BRIEF DESCRIPTION OF THE FIGURES

In the graphs in FIGS. 1-3, the x-as represents the number of weeks after birth in the life of an infant. The y-axis represents the z-score compared to the WHO Child Growth Standard of breastfed infants. Data points at 0, 17 weeks and 52 weeks are represented slightly shifted to one another so that the confidence intervals become visible.

EXAMPLES

Example 1: Experimental and Control Formula

Diet 1: Standard Nutrilon 1

Figure 1:
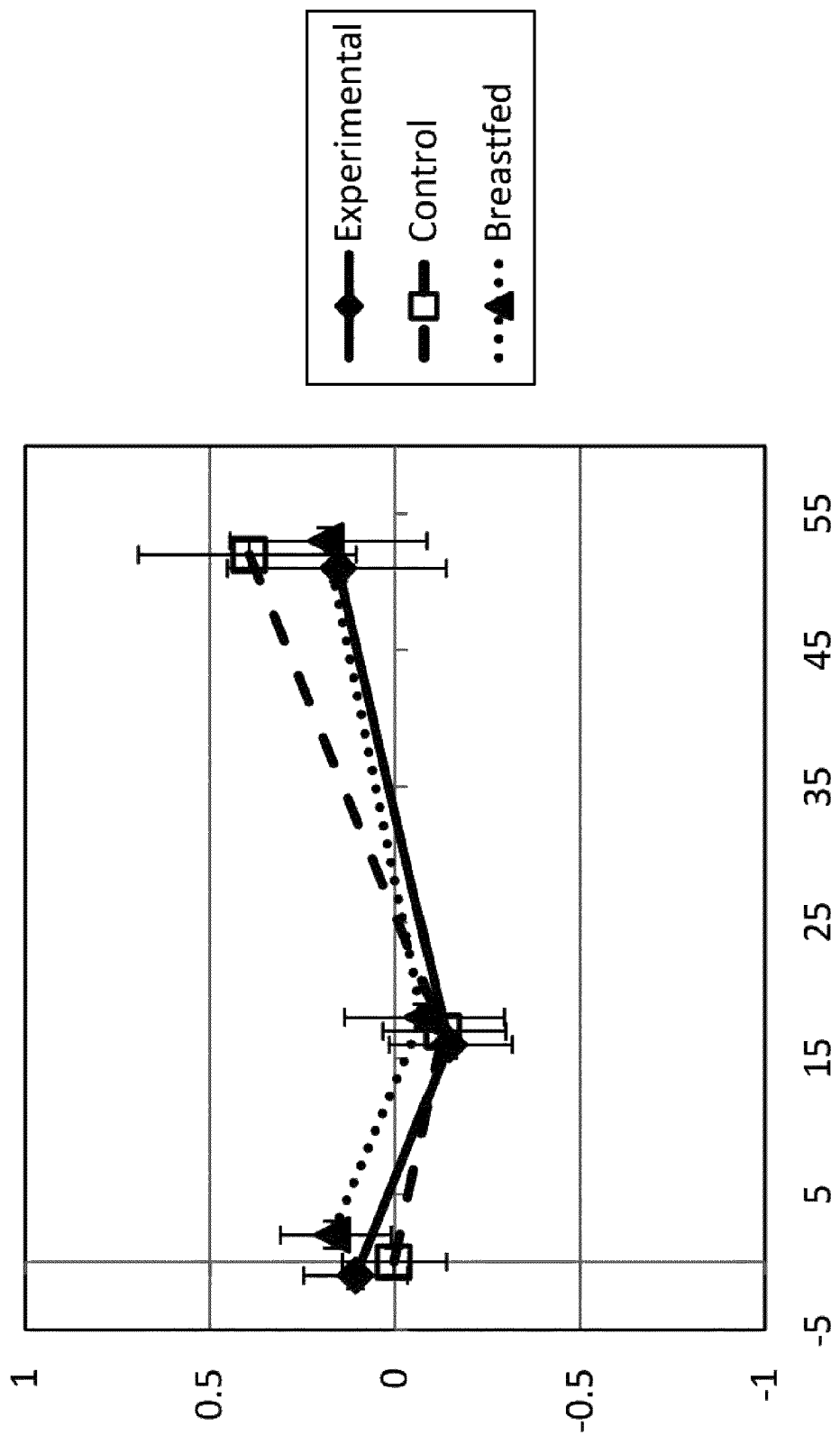
FIG. 1 shows mean and 95% confidence interval (CI) of weight-for-age-z-score, by age category, ITT group.

An infant formula with per 100 ml ready to drink formula 66 kcal, 1.3 g protein (whey protein and casein in a 6/4 w/w ratio), 7.3 g digestible carbohydrates (mainly lactose), 3.4 g fat and 0.8 g short chain galacto-oligosaccharides (source VivinalGOS) and long chain fructo-oligosaccharides (source RaftilinHP) in a 9/1 w/w ratio, and minerals, vitamins trace elements and other micronutrients as known in the art and in compliance with directives for infant formula. The formula is provided as a powder with the instruction to reconstitute with water. About 13.6 g powder was reconstituted to 100 ml ready to drink infant formula.

The lipid globules had a mode diameter, based on volume, of about 5.6 um, and the volume % of lipid globules with a mode between 2 and 12 μm was above 45.

The fat component comprised mainly vegetable fat (blend of palm oil, low erucic acid rape seed oil, coconut oil, high oleic sunflower oil, sunflower oil, a small amount of soy lecithin (0.13 wt. %) and about 1.5 wt. % of an LC-PUFA premix (fish oil and microbial oil).

The lipid globules had a mode diameter, based on volume, of about 0.5 μm, and the volume % of lipid globules with a mode between 2 and 12 μm was below 10.

Diet 2: Experimental Infant Formula

An infant formula similar as diet 1, except for the following: The fat component consisted of about 51 wt. % vegetable fat (blend of low erucic acid rape seed oil, coconut oil, high oleic sunflower oil, sunflower oil), about 44 wt. % bovine anhydrous milk fat, 1.5 wt. % LC-PUFA containing oil (fish oil and microbial oil), 0.13 wt. % soy lecithin, about 3.6 wt. % milk fat derived from buttermilk rich in milk phospholipids or milk fat globule membranes (milk phospholipids are about 1.5 wt. % based on total lipid).

The fatty acid composition is very similar between diet 1 and 2, in saturated, mono unsaturated and poly unsaturated acids, and in n3 and n6 PUFA content. The amount of palmitic acid was 18.4 wt. % and 17.7 wt. % (based on total fatty acids) for diet 1 and 2, respectively. For diet 2 about 36 wt. % of the palmitic acid residues was in the sn2 position, for diet 1 this was about 13 wt. %. The amount of C4:0 (butyric acid) was 0.10 wt. % in diet 1 and 1.39 wt. % in diet 2, C6:0 (caproic acid) was 0.24 wt. % in diet 1 and 0.98 wt. % in diet 2. The wt. % are based on total lipid in the infant formula.

Example 2: Study Protocol and Study Population

After parent(s)/legal guardian(s) have signed informed consent, exclusively formula fed infants eligible for participation were randomised to receive either the experimental product or the control product for a double-blind period of maximally 17 weeks (depending on their age at study entry). Exclusively breastfed infants participated in the reference group and had the same visit schedule and study assessments as the randomised infants. At the first visit, baseline and birth data were collected, and the study product and diaries were provided to the parent(s). Further study visits were conducted at 5, 8, 13 and 17 weeks of age. Information and anthropometrical measurements were collected during the visits. During the visit at 52 weeks (an optional extension of the study), anthropometrical measurements were collected. 4 countries with 17 sites participated, and in total 313 subjects were enrolled; 6 sites in the Netherlands (121 subjects), 3 sites in France (13 subjects), 7 sites in Belgium (158 subjects), and 1 site in Singapore (21 subjects). Of the total of 313 enrolled subjects, 223 were randomised and 88 were included in the breastfed reference group, 2 subjects were screen failures and were consequently not randomised.

The All-Subjects-Treated (AST) data set consisted of all subjects randomised (ASR, n=223) who received at least some study product. Subjects (n=8) with sufficient evidence that no study product was consumed were considered as non-treated, and were not included in the AST group (n=215).

The ITT data set consisted of all subjects from the ASR group (ITT=ASR). Results from the ITT analysis reflect the effects on the targeted population in a real clinical situation/ estimates the effect (effectiveness) of the treatment policy. Subjects' data were analysed 'as randomised'.

The Per-Protocol (PP) analysis restricts the analysis to the subjects who fulfil the protocol in the terms of the eligibility, interventions, instructions/restrictions and outcome assessment. The PP data set consisted of all subjects and/or subjects' visits from the ITT data set without any major protocol deviations. Thus, the PP dataset was not limited to subjects who completed the study, and the number of subjects per visits varies. Results from the PP analysis estimate the effect (efficacy) of the treatment. Subjects' data were analysed 'as treated'. The following rules have been applied for exclusion of subjects from the PP data set: Age at baseline (=visit 1) >35 days, birth weight missing or is <9.96th or >90.04th percentile (based on WHO Child growth standard references), Head circumference at inclusion is outside±2.04 SD percentile (based on WHO Child growth standard references), not having at least one valid post-baseline visit. Study product consumption started≥6 days after baseline, having received a different study product as his/her twin sibling, no study product was consumed, relevant medical history, i.e. illnesses/conditions as identified by the Medical Monitor. The following rules have been applied for exclusion of distinct visits from the PP data set: Any visit>3 days after stop of study product intake, regardless if stop was temporarily or not, any visit>3 days after start of other formula feeding, any visit>3 days after start of solid feeding. 49 randomised subjects plus certain visits were excluded.

For the non-randomised breastfed reference group data sets corresponding to the ITT and PP populations of the randomised infants have been defined, too. Correspondingly to the ITT data set, a full breast fed group (FBF) has been defined, no breast fed subjects were excluded. Correspondingly to the PP dataset, a Protocol Compliant Breastfed Reference (PCBF*) data set has been defined, applying the relevant rules as defined for the PP dataset. The following rules have been applied for exclusion of subjects from the PCBF data set: Age at baseline>35 days, birth weight missing or is <9.96th or >90.04th percentile (based on WHO Child growth standard references), Head circumference at inclusion is outside±2.04 SD (based on WHO Child growth standard references), not having at least one valid post-baseline visit, or relevant medical history, i.e. illnesses/ conditions as identified by the Medical Monitor. The following rules have been applied for exclusion of distinct visits from the PCBF data set: Any visit>3 days after stop of breastfeeding, in case stop of breastfeeding occurred before 13 weeks of age, any visit>3 days after start of other formula feeding, in case start of other formula feeding occurred before 13 weeks of age, any visit>3 days after start of solid feeding, in case start of other solid feeding occurred before visit 4. 11 breastfed subjects plus certain visits were excluded.

Subjects (either randomised or breastfed) who were included in PP/PCBF dataset up and including visit at 17 weeks of age and participated in the optional extension, were included in PP dataset at visit at 52 weeks.

There were no statistical significant differences between the intervention groups within different dataset (PP, ITT) on the stratification factors sex, age at baseline (<14 days/>14 days), regions (Europe vs. Asia). There was no difference in the duration in the study between the intervention groups.

The analysis of growth (weight and BMI at 52 weeks) was performed using parametric growth curves (PGC), correcting for the stratification factors described above. This approach assumes a parametric function of time (i.e. age of subject) and thus, describes the development of growth parameters (i.e. weight, BMI) over time by a second order polynomial function. It does not require the study subjects to be measured at the same set of time points. The resulting parameters are compared to assess differences between the curves. Sensitivity analyses to confirm model suitability were performed using General Linear Modelling (ANCOVA) and Arbitrary Mean Models, where time modelled as a categorical variable.

For the analysis of z-scores, each anthropometric measurement of subjects was normalized by using WHO Child growth standard z-score references which are age and gender dependent standardised values. A SAS macro (provided by WHO, http://www.who.int/childgrowth/software/en/) was used while normalizing the absolute anthropometric measurements of subjects, no correction for the stratification factors was performed. The analysis of z-scores was performed by age-category, selecting anthropometrical data collected within a window of ±10 days around a visit, taking the real age of the subjects into account. Age-categories are: Birth, 10±10 days at study entry, 35±10 days at week 5, 56±10 days at week 8, 91±10 days at week 13, 119±10 days at week 17, and 365±10 days at 52 weeks.

To conclude equivalence of weight gain from baseline visit (randomisation) until the age of 17 weeks in infants receiving the experimental product compared to infants receiving the control product, the two-sided 90% confidence intervals for the differences in mean weight gain should lie entirely between −0.5 SD and +0.5 SD margins, with a minimum of 3 g/d and a maximum of 5 g/d. The equivalence analysis was performed using parametric growth curves, correcting for the stratification factors described above. This approach assumes a parametric function of time (i.e. age of subject) and thus, describes the development of growth parameters (i.e. weight) over time by a second order polynomial function. It does not require the study subjects to be measured at the same set of time points. The resulting parameters are compared to assess differences between the curves. Sensitivity analyses to confirm model suitability were performed using General Linear Modelling (ANCOVA) and Arbitrary Mean Models, where time modelled as a categorical variable.

Example 3: Results Growth Trajectories and Body Development

Weight

The median weight (kg) of boys and of girls (included in the three study groups) was shown to be well within the z-score of −1 and +1 of the WHO Child growth standard z-scores, for the ITT and for the PP dataset (data not shown).

The weight gain per day in the experimental group was equivalent compared to the breastfed reference group (post hoc analysis) from visit at baseline until the age of 17 weeks, in the PP as well in the ITT datasets, using an equivalence margin of ±3 g/day. Equivalence of weight gain per day was demonstrated for the experimental formula compared to standard formula group (PP and ITT population), even when only selecting infants enrolled before 14 days of age.

The mean weight-for-age z-scores per visit and the corresponding 95% Confidence intervals (CI), showed that the growth in weight of the breastfed reference group was not different from the WHO Child growth standards. Between baseline and 13 weeks of age, the control group and experimental group showed a lower weight-for age z score than the WHO child growth standards for breastfed infants. For the ITT group the z scores of the experimental group were closer to the breast fed group, but the no statistical significant difference was suggested between the two groups (data not shown). At 17 weeks of age there were no statistically significant differences between the experimental or the control group and the WHO Child growth standards. In contrast, at 52 weeks of age the control group showed a significantly higher weight-for-age z-score compared to the WHO Child growth standards for breast fed infants. The experimental group was in particular at 52 weeks more similar to the breastfed reference group as indicated by the overlapping CI and for both groups there was no suggestion for a difference from the WHO Child growth standards. FIG. 1 shows the results obtained for the ITT dataset per age category (at birth, 17 and 52 weeks of age). The PP dataset showed similar results (data not shown).

Interestingly, although the effects were present both for girls and boys, the highest effect was observed for boys, both for PP and ITT group (data not shown).

At 52 weeks of age, the difference in weight between the study groups was compared using a PGC analysis, considering the overall study period (baseline until 52 weeks) and correcting for stratification factors. The results (in gram, for the overall period) as shown in Table 1 reveal that both for ITT and PP datasets the group that received the control formula has a higher weight, but no statistically significant different weight compared to the group receiving the experimental formula. However, the comparison of the control group with the breastfed reference group reveals a statistically significant higher weight in the control group for ITT and PP datasets, respectively (estimate of weight difference control vs. breastfed 551.09 g (p=0.0009) for ITT and 593.03 g (p=0.0009) for PP). The comparison of the experimental group with the breastfeed reference group showed higher weight in the experimental group, which was not statistically different for the PP dataset (estimate of weight difference 254.89 (p=0.1027). Compared to the control group, the experimental group was closer to the breast fed group.

TABLE 1

Differences in weight (grams) at 52 weeks between the study groups as by PGC analysis.

|  | ITT group estimates of the difference in weight (grams) at 52 weeks (p-value) | PP group estimates of the difference in weight (grams) at 52 weeks (p-value) |
| --- | --- | --- |
| Experimental vs Control | −190.11 (0.2524) | −350.50 (0.0580) |
| Experimental vs Breastfed | 357.53 (0.0254) | 254.89 (0.1027) |
| Control vs Breastfed | 551.09 (0.0009) | 593.03 (0.0009) |

PGC analysis, considering the overall study period (baseline until 52 weeks) and correcting for stratification factors.

BMI

The median BMI for boys and for girls included in the three study groups was well within the z-score of −1 and +1 of the WHO Child growth standard z-scores, for the ITT and the PP dataset (data not shown).

Figure 2:
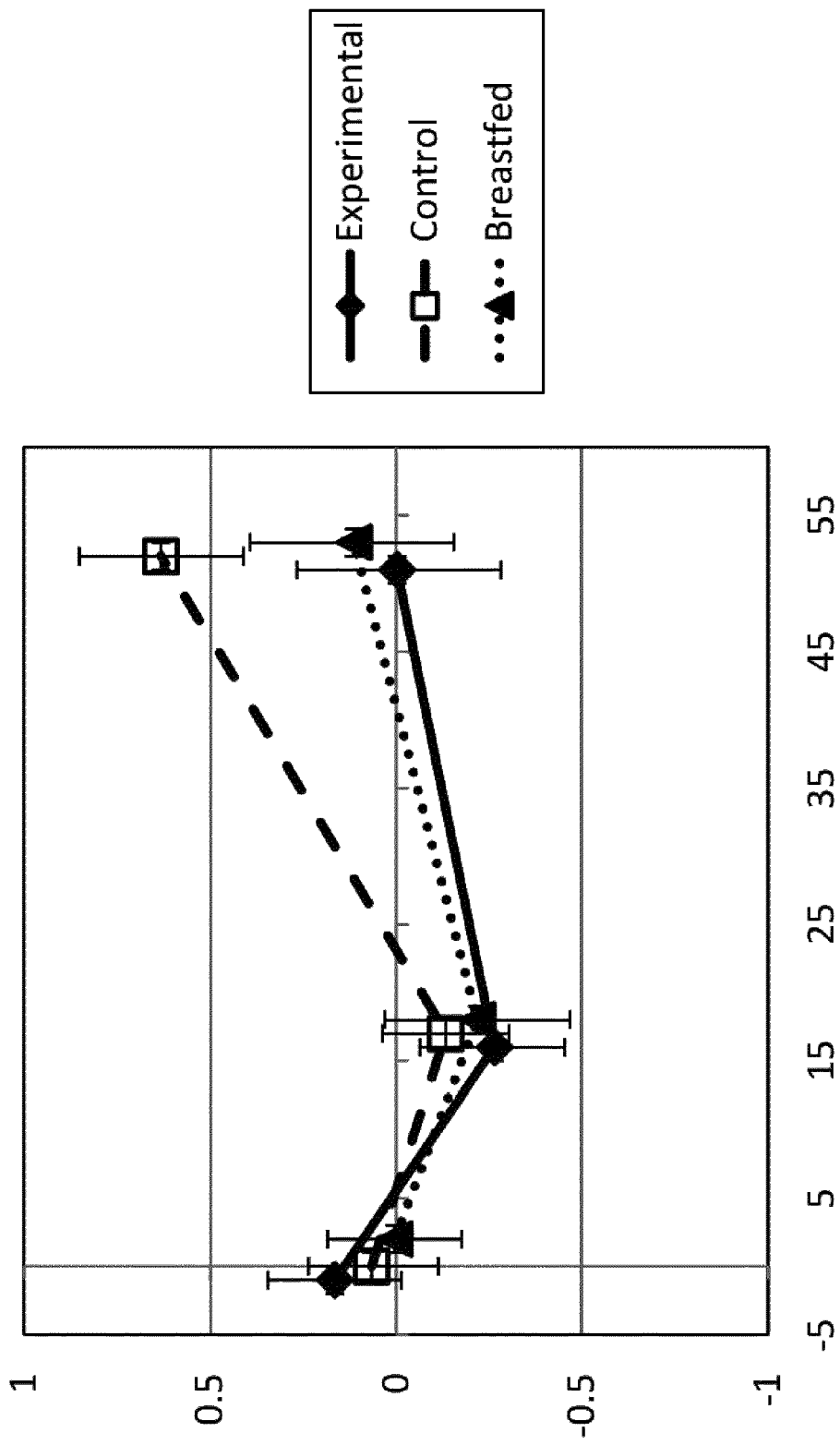
FIG. 2 shows mean and 95% CI of BMI-for-age z-score, by age category, ITT group.

The mean BMI-for-age z scores and the corresponding 95% Confidence intervals, showed that the growth in BMI of the breastfed reference group was not different from the WHO Child growth standards. For the ITT group at 17 weeks of age there was no statistical significant difference between the control group and the WHO Child growth standards, whereas the BMI z-score of the experimental group was lower and statistically significantly different compared to the WHO Child growth standards. In contrast, at 52 weeks of age the control group showed a significantly higher BMI-for-age z score compared to the WHO Child growth standards off breastfed infants The experimental group on the other hand was more similar to the breastfed reference group as indicated by the overlapping CI and for both groups there was no significant difference from the WHO Child growth standards. FIG. 2 shows the results obtained for the ITT dataset. The PP dataset showed similar results (data not shown). Interestingly, although the effects were present both for girls and boys, the highest effect was observed for boys, both for PP and ITT group (data not shown).

At 52 weeks of age, the difference in BMI between the study groups was compared using a PGC analysis, considering the overall study period (baseline until 12 months) and correcting for stratification factors. The results as shown in Table 2 reveal that both for ITT and PP datasets the group that received the control formula had the highest BMI, which was statistically significant different compared to the group receiving the experimental formula and compared to the breastfed reference group. The comparison of the experimental group with the breastfeed reference group showed higher, but not statistically significant different BMI in the experimental group, neither for the ITT nor the PP dataset.

TABLE 2

Differences in BMI (kg/m$^2$) at 52 weeks between the study groups as by PGC analysis

|  | ITT group estimates of the difference in BMI at 52 weeks (p-value) | PP group estimates of the difference in BMI at 52 weeks (p-value) |
| --- | --- | --- |
| Experimental vs. Control | −0.80 (0.0006) | −0.89 (0.0014) |
| Experimental vs. Breastfed | 0.41 (0.0682) | 0.42 (0.0727) |
| Control vs. Breastfed | 1.22 (<.0001) | 1.30 (<.0001) |

PGC analysis, considering the overall study period (baseline until 12 months) and correcting for stratification factors Weight-for-Length The median weight-for-length of boys and girls (included in the three study groups was well within the z-score of −1 and +1 of the WHO Child growth standard z-scores, for the ITT and the PP dataset (data not shown).

In line with BMI-for age z-scores, none of the study group reveals a weight-for-length z-score at birth which was significantly different from the WHO Child growth standards. The mean weight-for-length z-scores of the experimental group was slightly lower and significantly different from the WHO Child growth at 17 weeks of age.

Figure 3:
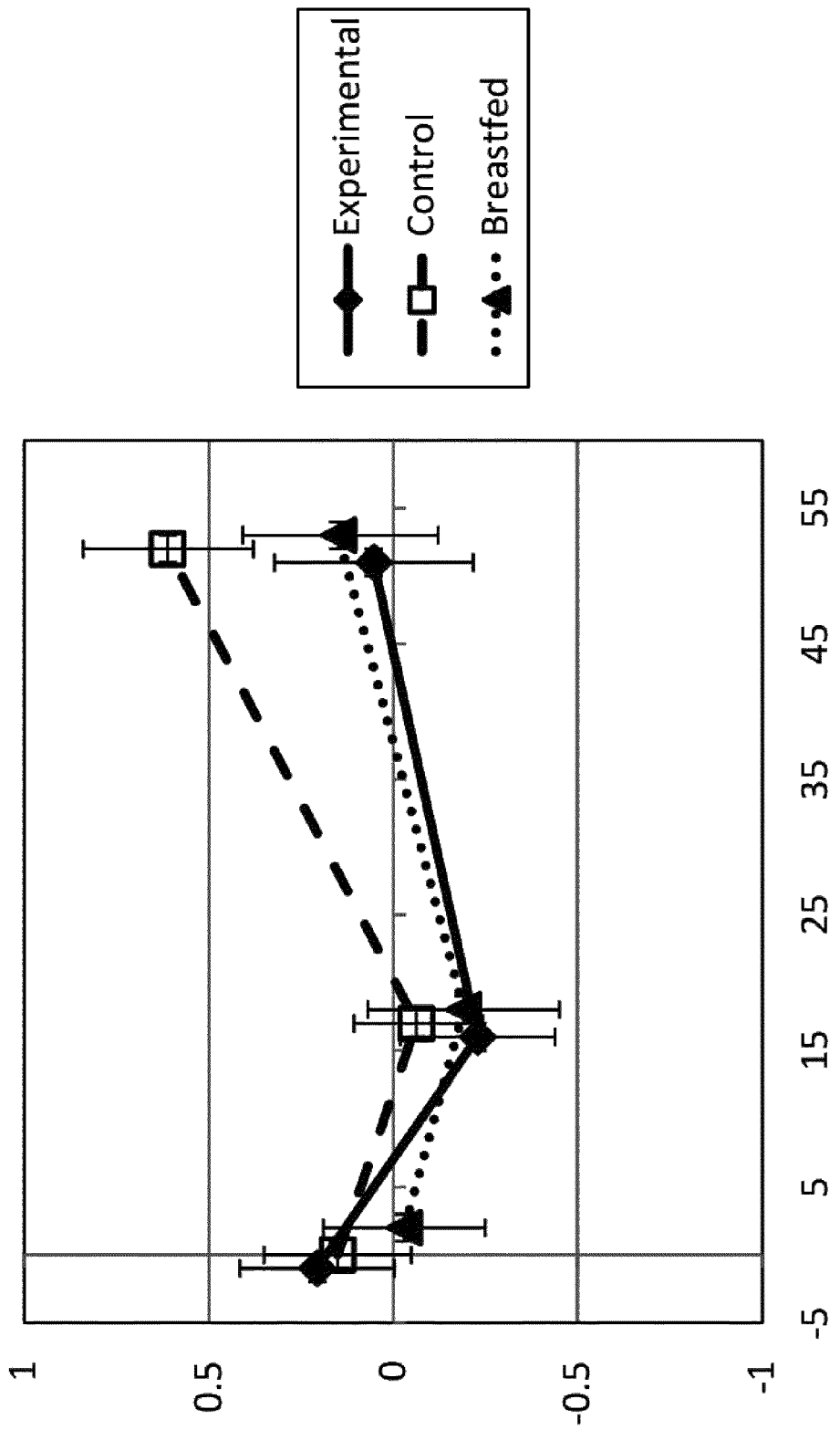
FIG. 3 shows mean and 95% CI of weight-for-length z-score, by age category, ITT group. In the examples data is collected at 17 weeks and at 52 weeks of age. This is interpreted as corresponding to 4 months and 12 months of age respectively. In other words, in the context of the present invention, 4 months of age is considered the same as 17 weeks of age and 12 months of age is considered the same as 52 weeks of age.

At 52 weeks of age there were not differences between the experimental group and the WHO Child growth standards anymore. On the contrary the mean weight-for-length z-scores of the control group at 52 weeks age was higher and significantly different from the WHO Child growth standards. FIG. 3 shows the results obtained for the ITT dataset. The PP dataset showed similar results (data not shown).

Interestingly, although the effects were present both for girls and boys, the highest effect was observed for boys, both for PP and ITT group (data not shown).

It should be noted that the difference between the control formula and the breastfed reference group are in line with the observations found in in the scientific literature when comparing breast fed infants with formula fed infants (Dewey et al., 1993, Am J Clin Nutr 57: 140-145).

All mean values (for weight, BMI, weight for length, head circumference and skin folds) are well within the range of normal, healthy infants who are not at risk of obesity.

Skinfold Thickness and Head Circumference

Skinfold thickness is a non invasive measurement of body fat in infants and is an indication of the body development. At 52 weeks the biceps, triceps, suprailiac and subscapular skinfolds were determined, as well as the sum of these skinfolds. The skinfolds of the breast fed reference group (ITT) were lower in case of the biceps, triceps, suprailiac and sum of skinfolds, and were higher for the subscapular skinfold when compared with the control group. In all cases the skinfolds of the experimental group was intermediate, and closer to the breast fed reference group than the control group. The triceps and subscapular skinfold z score of the breast fed reference group was closest to the WHO Child growth standard of human milk infants, and also all the skinfolds in the experimental group were closer to the WHO Child growth standard than the control group.

Also the head circumference-by-age z-score of the experimental group (ITT) was very similar to that of the breastfed reference group, and similar to the WHO Child growth standard of breast fed infants. The z score of the control group (ITT) on the other hand was higher at 12 months of age than the other two groups and was significantly higher that the WHO Child growth standard.

These results are indicative for an effect of formula for infants on promoting a postnatal growth trajectory or body development in an infant towards a growth trajectory or body development which is similar to the growth trajectory or body development observed in human milk fed infants and/or on promoting a postnatal growth trajectory or body development in an infant towards a growth trajectory or body development which is closer to the optimal growth trajectory or body development of the WHO Child Growth Standards of human milk fed infants. Also these results are indicative for an effect of formula for infants on improving the postnatal growth trajectory or body development in an infant towards the growth trajectory or body development observed in human milk fed infants, in particular when compared to the growth trajectory or body development in infants fed infant formula of follow on formula comprising lipid globules of about 0.5 µm and that do not have a coating of phospholipids. Further these results are indicative for an effect of formula for infants on promoting a balanced growth trajectory or body development in an infant and/or preventing or reducing the risk of an unbalanced growth trajectory or body development in an infant.

The invention claimed is:

1. A method of improving postnatal growth trajectory towards a growth trajectory observed in human breastfed healthy term born infants when compared to the growth trajectory in healthy term born infants fed infant formula or follow on formula comprising lipid globules of about 0.5 µm and that do not have a coating of phospholipids, wherein the growth trajectory is over the first 12 months of life of the healthy term born infant, and wherein at 12 months:
 (i) the healthy term born infant has a weight and/or BMI and/or weight for length that is not statistically different from the weight and/or BMI and/or weight for length at 12 months of human breastfed infants, and/or
 (ii) the healthy term born infant has a head circumference that is not statistically different from the head circumference at 12 months of human breastfed infants, and/or
 (iii) the healthy term born infant has a skinfold thickness that is not statistically different from the skinfold thickness at 12 months of human breastfed infants,
 the method comprising administering to a healthy term born infant an infant formula and/or a follow on formula comprising:
 (a) 3 to 7 g lipid/100 kcal, 1.25 to 5 g protein/100 kcal and 6 to 18 g digestible carbohydrate/100 kcal; and
 (b) lipid globules having (i) mode diameter, based on volume of at least 1.0 µm and/or having a diameter of 2 to 12 µm in an amount of at least 45 volume % based on total lipid, and/or (ii) on the surface at least partly a coating of phospholipids.

2. The method according to claim 1, wherein the skinfold thickness is subscapular skinfold thickness and/or triceps skinfold thickness.

3. The method according to claim 1, wherein the healthy term born infant is a male healthy term born infant.

4. The method according to claim 1, wherein the lipid globules have (i) a mode diameter, based on volume of at least 1.0 µm and a diameter of 2 to 12 µm in an amount of at least 45 volume % based on total lipid.

5. The method according to claim 1, wherein the formula comprises at least 0.5 wt. % phospholipids based on total lipid.

6. The method according to claim 1, wherein the phospholipids comprise at least 15 wt. % sphingomyelin based on total phospholipids.

7. The method according to claim 1, wherein the lipid comprises triglycerides that comprise at least 10 wt. % palmitic acid based on total fatty acids, and wherein at least 15% of the palmitic acid is present at the sn-2 position of the triglycerides.

8. The method according to claim 1, wherein the formula is a powder, suitable to reconstitute with water to provide a ready to drink formula.

9. The method according to claim 1, wherein at 12 months the healthy term born infant has a weight and/or BMI and/or weight for length that is not statistically different from the weight and/or BMI and/or weight for length at 12 months according to WHO Child Growth Standards of human breastfed infants, wherein the WHO Child Growth Standards of human breastfed infants refers to the WHO Child Growth Standards published in Acta Paediatrica, April 2006, volume 95, supplement 450.

10. The method according to claim 1, wherein at 12 months the healthy term born infant has a head circumference that is not statistically different from the head circumference at 12 months according to WHO Child Growth Standards of human breastfed infants, wherein the WHO Child Growth Standards of human breastfed infants refers to the WHO Child Growth Standards published in Acta Paediatrica, April 2006, volume 95, supplement 450.

11. The method according to claim 1, wherein at 12 months the healthy term born infant has a skinfold thickness that is not statistically different from the skinfold thickness at 12 months according to WHO Child Growth Standards of human breastfed infants, wherein the WHO Child Growth Standards of human breastfed infants refers to the WHO Child Growth Standards published in Acta Paediatrica, April 2006, volume 95, supplement 450.

12. A method of improving postnatal body development towards a body development observed in human breastfed healthy term born infants when compared to the body development in healthy term born infants fed infant formula or follow on formula comprising lipid globules of about 0.5 µm and that do not have a coating of phospholipids, wherein the body development is over the first 12 months of life of the healthy term born infant, and wherein at 12 months:
 (i) the healthy term born infant has a weight and/or BMI and/or weight for length that is not statistically different from the weight and/or BMI and/or weight for length at 12 months of human breastfed infants, and/or
 (ii) the healthy term born infant has a head circumference that is not statistically different from the head circumference at 12 months of human breastfed infants, and/or
 (iii) the healthy term born infant has a skinfold thickness that is not statistically different from the skinfold thickness at 12 months of human breastfed infants,
 the method comprising administering to a healthy term born infant an infant formula and/or a follow on formula comprising:
   (a) 3 to 7 g lipid/100 kcal, 1.25 to 5 g protein/100 kcal and 6 to 18 g digestible carbohydrate/100 kcal; and
   (b) lipid globules having (i) mode diameter, based on volume of at least 1.0 µm and/or having a diameter of 2 to 12 µm in an amount of at least 45 volume % based on total lipid, and/or (ii) on the surface at least partly a coating of phospholipids.

13. The method according to claim 12, wherein the skinfold thickness is subscapular skinfold thickness and/or triceps skinfold thickness.

14. The method according to claim 12, wherein the healthy term born infant is a male healthy term born infant.

15. The method according to claim 12, wherein the lipid globules have (i) a mode diameter, based on volume of at least 1.0 µm and a diameter of 2 to 12 µm in an amount of at least 45 volume % based on total lipid.

16. The method according to claim 12, wherein the formula comprises at least 0.5 wt. % phospholipids based on total lipid.

17. The method according to claim 12, wherein the phospholipids comprise at least 15 wt. % sphingomyelin based on total phospholipids.

18. The method according to claim 12, wherein the lipid comprises triglycerides that comprise at least 10 wt. % palmitic acid based on total fatty acids, and wherein at least 15% of the palmitic acid is present at the sn-2 position of the triglycerides.

19. The method according to claim 12, wherein the formula is a powder, suitable to reconstitute with water to provide a ready to drink formula.

20. The method according to claim 12, wherein at 12 months the healthy term born infant has a weight and/or BMI and/or weight for length that is not statistically different from the weight and/or BMI and/or weight for length at 12 months according to WHO Child Growth Standards of human breastfed infants, wherein the WHO Child Growth Standards of human breastfed infants refers to the WHO Child Growth Standards published in Acta Paediatrica, April 2006, volume 95, supplement 450.

21. The method according to claim 12, wherein at 12 months the healthy term born infant has a head circumference that is not statistically different from the head circumference at 12 months according to WHO Child Growth Standards of human breastfed infants, wherein the WHO Child Growth Standards of human breastfed infants refers to the WHO Child Growth Standards published in Acta Paediatrica, April 2006, volume 95, supplement 450.

22. The method according to claim 12, wherein at 12 months the healthy term born infant has a skinfold thickness that is not statistically different from the skinfold thickness at 12 months according to WHO Child Growth Standards of human breastfed infants, wherein the WHO Child Growth Standards of human breastfed infants refers to the WHO Child Growth Standards published in Acta Paediatrica, April 2006, volume 95, supplement 450.

\* \* \* \* \*